United States Patent [19]

Corbett et al.

[11] Patent Number: 4,477,662

[45] Date of Patent: Oct. 16, 1984

[54] 2-SUBSTITUTED THIO CARBAPENEM DERIVATIVES

[75] Inventors: David F. Corbett, Reigate; Pamela Brown née Davis, Guildford; Roger J. Ponsford, Horsham, all of England

[73] Assignee: Beecham Group p.l.c., England

[21] Appl. No.: 345,484

[22] Filed: Feb. 3, 1982

[30] Foreign Application Priority Data

Feb. 4, 1981 [GB] United Kingdom ............... 8103350

[51] Int. Cl.³ ............................................ C07D 487/04
[52] U.S. Cl. .................................... 544/212; 544/182; 544/198; 544/209; 544/215; 544/219; 544/298; 544/316; 544/319; 546/272; 548/252; 548/253; 548/336; 260/245.2 T; 260/245.2 R
[58] Field of Search ................ 260/245.2 T; 546/272; 544/298, 316, 319, 219, 182, 212, 198, 209, 215; 548/252, 253, 336

[56] References Cited

U.S. PATENT DOCUMENTS 4,337,199 6/1982 Yoshioka et al. ............ 260/245.2 T

*Primary Examiner*—Nicholas S. Rizzo
*Attorney, Agent, or Firm*—Jacobs & Jacobs

[57] ABSTRACT

A process for the preparation of an antibacterially active compound of the formula (I):

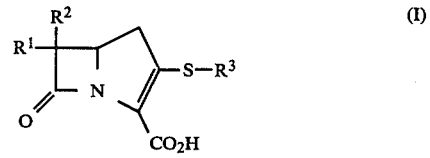

and salts and esters thereof wherein $R^1$ and $R^2$ independently are hydrogen or an organic group, and $R^3$ is an organic group bonded via a carbon atom to the sulphur atom, which comprises reacting a compound of the formula (II):

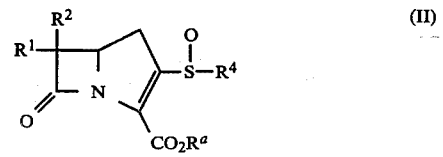

wherein $R^4$ is an organic group different to $R^3$ and $R^a$ is hydrogen or a carboxy-blocking group, with a thiol $R^3SH$ or reactive derivative thereof. In addition certain compounds within the formula (II) are novel and useful antibacterial agents in their own right.

16 Claims, No Drawings

2-SUBSTITUTED THIO CARBAPENEM DERIVATIVES

This invention relates to a chemical process for preparing carbapenem derivatives and in particular to 2-substituted thio carbapenem derivatives. These carbapenems are useful in the treatment of antibacterial infection either alone or in combination with other therapeutic agents.

The present invention provides a process for the preparation of a compound of the formula (I):

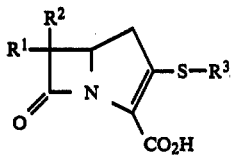

and pharmaceutically acceptable salts and in-vivo hydrolysable esters thereof wherein $R^1$ and $R^2$ each represent a hydrogen atom or an organic group, and $R^3$ represents an organic group bonded via a carbon atom to the sulphur atom; which process comprises reacting a compound of the formula (II):

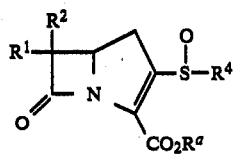

wherein $R^a$ is a carboxy-blocking group or a hydrogen atom, and $R^1$ and $R^2$ are as defined in relation to formula (I) and $R^4$ represents an organic group different to the group $R^3$, with the exception that $R^4$ is not a group $-CH_2CH_2-R^5$ wherein $R^5$ is an amino, protected amino, alkylamino or acylamino moiety; and a compound of the formula (III):

 $R^3-SH$       (III)

or reactive derivative thereof, wherein $R^3$ is as defined in relation to formula (I); and thereafter if necessary:
 (i) removing any carboxy-blocking group $R^a$,
 (ii) converting the product into a pharmaceutically acceptable salt or in-vivo hydrolysable ester.

The process of this invention may be carried out in any solvent that is substantially inert during the reaction for example tetrahydrofuran, dimethylformamide, dioxan, hexamethyl phosphoramide, dimethoxyethane or dimethoxydiethyl ether. Of these solvents dimethylformamide is preferred.

Alternatively we have found it useful to use a phase transfer catalyst. Particularly suitable phase transfer catalysts include tetra-n-butyl ammonium bromide, cetyldimethylbenzylammonium chloride and cetyltriethyl ammonium chloride. Suitable solvents include halogenated water-immiscible solvents such as chloroform or dichloromethane in the presence of water.

The reaction is normally performed at ambient or a depressed temperature, for example 20° C. to −70° C., and preferably between 0° C. and −50° C. However when using a phase transfer catalyst it is preferable to conduct the reaction between 0° C. and ambient temperature.

When the thiol compound of the formula (III) is used, the reaction is normally carried out in the presence of a base. Examples of such bases include sodium hydride, sodium hydroxide, sodium alkoxide such as the methoxide, ethoxide or butoxide, sodium amide, potassium hydroxide, potassium alkoxide such as the methoxide, ethoxide or butoxide, potassium amide, and trialkylamines such as triethylamine and tri-n-propylamine. Of these triethylamine is preferred. Preferably the base is present in an amount of at least 0.9 equivalents, more preferably between 1.0 and 1.2 equivalents, per mole of the thiol compound.

Instead of using a base in the reaction, a reactive derivative of the thiol may be used, preferably the reactive derivative is a salt of the thiol, in particular an alkali metal salt such as sodium, potassium or lithium.

The amount of thiol compound of the formula (III) or reactive derivative thereof is generally between 1.0 and 1.5 moles per mole equivalent of the compound of the formula (II).

The group $R^3$ in the compound of the formula (I) may be $C_{1-6}$ alkyl, $C_{2-6}$ alkenyl, $C_{2-6}$ alkynyl, aryl $(C_{1-6})$ alkyl, $C_{1-6}$ alkanoyl, aryl $(C_{1-6})$ alkanoyl, arylcarbonyl, aryl, heterocyclyl, heterocyclyl $(C_{1-6})$ alkyl, heteroaryl $(C_{1-6})$ alkyl or heteroaryl group, any of such groups being optionally substituted. Suitably the hetero atom or hetero atoms in the above named heteroaryl and/or heterocyclyl moieties are selected from 1 to 4 oxygen, nitrogen or sulphur atoms.

Suitable optional substituents for the group $R^3$ include amino, alkanoylamino, mono, di- and tri-alkylamino, hydroxy, alkoxy, mercapto, alkylthio, arylthio, sulphamoyl, carbamoyl, amidino, guanidino, nitro, chloro, bromo, fluoro, carboxy and salts and esters thereof, alkanoyloxy, arylcarbonyl and heteroarylcarbonyl.

Suitably $R^3$ is $C_{1-6}$ alkyl, $C_{2-6}$ alkenyl, aryl such as phenyl, aralkyl wherein the aryl moiety is preferably phenyl and the alkyl part has 1 to 6 carbon atoms, for example benzyl, phenethyl; heterocyclyl or heterocyclylalkyl wherein the alkyl part has 1 to 3 carbon atoms and the heterocyclic ring comprises 4 to 7 atoms, preferably 5 to 6, up to 4 of which may be selected from oxygen, sulphur and nitrogen, such as pyridyl, furyl, thienyl, pyrimidinyl, imidazolyl, triazinyl and tetrazolyl.

Preferably $R^3$ is $C_{1-6}$ alkyl for example methyl, ethyl or propyl, optionally substituted by amino, alkanoylamino, carboxy, mono- and di-alkylamino, hydroxy or $C_{1-6}$ alkoxy; $C_{2-6}$ alkenyl such as vinyl optionally substituted with alkanoylamino such as acetamido or carboxy or salt or ester thereof; or is an optionally substituted phenyl, pyrimidinyl or pyridyl group.

Preferably in the compounds of the formulae (I) and (II) either $R^1$ or $R^2$ is a hydrogen atom. In an alternative aspect both $R^1$ and $R^2$ are hydrogen atoms.

When the group $R^1$ or $R^2$ represents an organic radical, it may be substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkynyl wherein the aryl moiety is phenyl and the linear chain has 1–6 carbon atoms; heteroaryl, heteroaralkyl, heterocyclyl and heterocyclylalkyl wherein the substituent or substituents relative to the above-named radicals are selected from the group consisting of: amino, mono-, di- and tri-alkylamino, hydroxyl, alkoxyl, mercapto, alkylthio, arylthio such as phenylthio, sulfamoyl, amidino, guanidino, nitro, chloro, bromo, fluoro, cyano and carboxy, and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms.

Preferably one of $R^1$ and $R^2$ is a hydrogen atom and the other is sulphonato-oxyethyl or hydroxyalkyl containing up to 6 carbon atoms, in particular α-hydroxyethyl or α-hydroxypropyl.

Suitably in the compounds of the formula (II) $R^4$ is a group as described in relation to $R^3$ in formula (I). More suitably $R^4$ is a $C_{1-6}$ alkyl, $C_{2-6}$ alkenyl, aryl or heteroaryl group, any of such groups being optionally substituted. Preferably $R^4$ is methyl, ethyl, alkanoylaminoethenyl such as acetamidoethenyl, phenyl, pyridyl or pyrimidinyl.

It will be realised to those skilled in the art that the sulphoxides of the formula (II) may exist in either the α- or β-configuration, that is to say as either formula (IV) or (V):

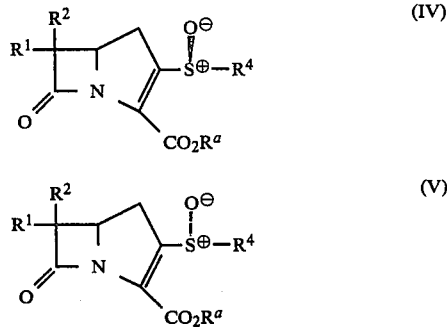

wherein $R^1$, $R^2$, $R^4$ and $R^a$ are as hereinabove defined. Both these configurations, either separated or mixed, are within the ambit of this invention.

In the compounds of the formulae (I) and (III), if $R^1$ is a hydrogen atom and $R^2$ is not a hydrogen atom, or vice versa, then cis- and trans-configurations of hydrogen atoms about the β-lactam exist. Both configurations, either separated or mixed, are within the ambit of this invention.

Suitable carboxyl-blocking derivatives for the group —$CO_2R^a$ in formula (II) include salts, esters, and anhydride derivatives of the carboxylic acid. The derivative is one which may readily be cleaved at a later stage of the reaction. The salts need not be pharmaceutically acceptable. Suitable salts include inorganic salts, for example metal salts such as silver or mercuric salt, or alkali metal salts such as the lithium or sodium salt, tertiary amine salts, such as those with tri-lower-alkylamines, N-ethylpiperidine, dimethylpiperazine. A preferred salt is with triethylamine.

Suitable ester-forming carboxyl-blocking groups are those which may be removed under conventional conditions. Such groups for $R^a$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula —N=CHR° where R° is aryl or hetero-cyclic, or an in vivo hydrolysable ester.

The carboxyl group may be regenerated from any of the above esters by usual methods appropriate to the particular $R^a$ group, for example, acid- and base-catalysed hydrolysis, or by enzymically-catalysed hydrolysis, or by hydrogenation. The hydrolysis must of course be carried out under conditions to which the groups on the rest of the molecule are stable.

When it is desired to produce a compound of formula (I) in the form of a free acid or salt by the process of this invention, a compound of formula (II) is generally employed wherein $R^a$ is a carboxyl-blocking group. For the preparation of a compound of formula (I) in the form of a pharmaceutically acceptable ester, it is convenient to employ a compound of formula (II) wherein $R^a$ represents the desired ester group.

Preferably the process of this invention is performed on a compound of the formula (II) wherein $R^a$ is an ester-forming group.

Suitable esters of the compounds of the formula (II) for use in the process of this invention include those cleavable by biological methods and by chemical methods such as hydrogenolysis, hydrolysis, electrolysis or photolysis.

Suitably the carboxylic acid is esterified by a group of the sub-formula (a), (b), (c) or (d):

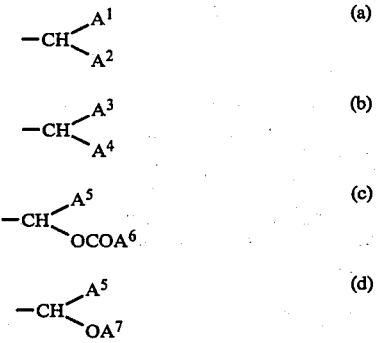

wherein $A^1$ is a hydrogen atom, $O_{1-6}$ alkanoyl or an alkyl, alkenyl or alkynyl group of up to 3 carbon atoms; $A^2$ is a hydrogen atom or a methyl group; $A^3$ is a phenyl group or a phenyl group substituted by a fluorine, chlorine or bromine atom or a nitro, methyl or methoxy group; $A^4$ is a hydrogen atom or a phenyl group or a phenyl group substituted by a fluorine, chlorine or bromine atom or a nitro, methyl or methoxy group; $A^5$ is a hydrogen atom or a methyl group; $A^6$ is a $C_{1-4}$ alkyl, phenyl or $C_{1-4}$ alkoxy group or $A^5$ is joined to $A^6$ to form a phthalidyl, dimethylphthalidyl or dimethoxyphthalidyl group; and $A^7$ is a $C_{1-4}$ alkyl, phenyl, chlorophenyl or nitrophenyl group; or $CHA^1A^2$ is a phenacyl or bromophenacyl group.

Favourably $A^1$ is a hydrogen atom or a methyl, ethyl, vinyl or ethenyl group. Favourably $A^2$ is a hydrogen atom. Favourably $A^3$ is a phenyl, p-bromophenyl, p-methoxyphenyl or p-nitrophenyl group. Favourably $A^4$ is a hydrogen atom. Favourably $A^6$ is a methyl, t-butyl or ethoxy group or is joined to $A^5$. Favourably $A^7$ is a methyl group.

Preferred groups of the sub-formula (a) include the methyl, ethyl and acetonyl groups.

Preferred groups of the sub-formula (b) include the benzyl and p-nitrobenzyl groups.

Preferred groups of the sub-formula (c) include the acetoxymethyl, pivaloyloxymethyl, α-ethoxycarbonyloxymethyl and phthalidyl groups.

A preferred group of the sub-formula (d) is the methoxymethyl group.

Particularly preferred esterifying groups are the p-nitrobenzyl and phthalidyl groups.

Pharmaceutically acceptable in-vivo hydrolysable esters are those esters which hydrolyse in the human body to produce the parent acid or its salt. Such esters may be identified by administration to a test animal such as a rat or mouse by intravenous administration and thereafter examining the test animal's body fluids for the presence of the compound of the formula (I) or its salt.

Suitable esters of this type include those of subformula (c) as hereinbefore defined.

Suitable pharmaceutically acceptable salts include those of the alkali and alkaline earth metals, of these the sodium and potassium salts are preferred. These pharmaceutically acceptable salts may be formed at the C-2 carboxy and/or at the C-6 sulphonato-oxyethyl moiety (if present). Thus compounds of the formula (I) wherein $R^1$ contains a $-OSO_3H$ group or pharmaceutically acceptable salt thereof, may be in the form of a di-salt such as the di-sodium or dipotassium salt, or may be in the form of a mono-salt of an in-vivo hydrolysable ester, or may be in the form of a mono-salt of an acid or may be in the form of a di-acid.

Non-pharmaceutically acceptable salts of compounds of the formula (I) are also of use as they may be converted to pharmaceutically acceptable salts or in-vivo hydrolysable esters. An example of such a salt is the lithium salt.

Esters may be converted to the free acid or a salt of the formula (I) by methods appropriate to the particular ester, for example by acid- and base-catalysed hydrolysis or by enzymically-catalysed hydrolysis or via hydrogenolysis, electrolysis or photolysis. The conditions selected must of course not cause substantial degradation of the rest of the molecule.

Compounds of the formula (I) when in the form of an in-vivo hydrolysable ester, may be prepared from the free acid or salt thereof by esterifications using methods known to those skilled in the art. A convenient method is often reaction with a reactive halide, for example bromophthalide in solution in a polar orgnic solvent such as dimethylformamide.

The compounds of the formula (II) may be prepared by the methods of European Patent Application Publication No. 0002564.

Alternatively the compounds of the formula (II) may be prepared by the S-oxidation of a compound of the formula (VI):

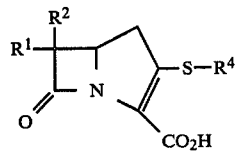

(VI)

or salt or ester thereof wherein $R^1$, $R^2$ and $R^4$ are as defined in relation to formula (II) with an oxidising agent; and thereafter if necessary converting the free acid or salt to an ester.

Suitable oxidising agents include perbenzoic acid, hydrogen peroxide, iodobenzene dichloride/water and sodium metaperiodate. Substituted perbenzoic acids such as m-chloroperbenzoic acid are preferred.

The reaction between the compound of the formula (VI) and the oxidising agent is conveniently performed in an inert solvent such as methylene chloride, chloroform/ethanol, aqueous dioxan, chloroform or carbon tetrachloride at an ambient or depressed temperature, preferably between $-30°$ C. and $+20°$ C.

The amount of the oxidising agent used in the oxidation of the compound of the formula (VI) can vary widely dependent on the type of oxidising agent, reaction conditions, presence of other potentially reactive groups, etc. Generally between 1 and 2 molar equivalents of the oxidising agent are preferred.

After the reaction the sulphoxide of the formula (II) may be isolated by known methods if desired.

Certain of the compounds of the formula (VI) are novel, and these compounds have antibacterial and β-lactamase inhibitory properties in their own right.

Thus the present invention provides the compounds of the formula (VII):

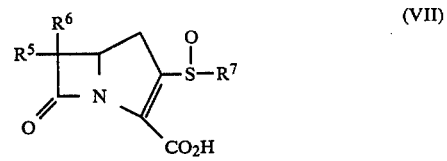

(VII)

and pharmaceutically acceptable salts and in-vivo hydrolysable esters thereof, wherein:

(a) $R^5$ is a group $R^1$ as defined in formula (I) except that it is not hydrogen, $R^6$ is a group $R^2$ as defined in formula (I) except that it is not hydrogen and $R^7$ is a group $R^4$ as hereinbefore defined, or (b) $R^5$ and $R^6$ are groups $R^1$ and $R^2$ respectively as defined in relation to formula (I), and $R^7$ is a heteroaryl group, or (c) $R^5$ and $R^6$ are groups $R^1$ and $R^2$ respectively as defined in relation to formula (I), and $R^7$ is an optionally substituted $C_{1-6}$ alkyl, $C_{2-6}$ alkenyl or aryl group, with the proviso that the compounds are in the free acid form or pharmaceutically acceptable salt thereof, with the further proviso that when $R^1$ is hydrogen and $R^2$ is αhydroxyethyl, α-hydroxypropyl, α-sulphonato-oxyethyl or α-sulphonato-oxypropyl $R^7$ is not acetamidoethenyl or acetamidoethyl and when $R^1$ is hydrogen and $R^2$ is ethyl or isopropyl $R^7$ is not acetamidoethyl.

Suitably the hetero atom or hetero atoms in the above named heteroaryl moiety are selected from 1 to 4 oxygen, nitrogen or sulphur atoms. Such heteroaryl moieties may be optionally substituted with substituents as described hereinbefore with reference to $R^3$.

Similarly suitable substituents for $C_{1-6}$ alkyl, $C_{2-6}$ alkenyl and aryl in variant (c) above include those described hereinbefore with reference to $R^3$.

Preferably $R^7$ is an optionally substituted pyridyl or pyrimidyl group.

Thus in a further aspect of this invention there is provided a pharmaceutical composition which comprises a compound of the formula (VII) or pharmaceutically acceptable salt or in vivo hydrolysable ester thereof and a pharmaceutically acceptable carrier.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit dose composition adapted for administration by injection.

Unit-dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 Kg adult is about 200 to 2000 mg, for example about 400, 600, 750, 1000 or 1500 mg.

The compositions of this invention may be used to treat infections of the respiratory tract, urinary tract or soft tissues in animals including humans, or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato starch or polyvinylpolypyrrolidone, magnesium stearate or sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin or mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride and bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium amplicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly, suitable cephalosporins for inclusions in the injectably administrable compositions of this invention include cephaloridine, cefazolin and cephradine, generally as their pharmaceutically acceptable salt.

The weight ratio between compound of this invention and penicillin or cephalosporin is generally from 10:1 to 1:10, more usually from 5:1 to 1:5 and normally from 3:1 to 1:3.

The penicillin or cephalosporin is generally utilised in its conventionally administered amount.

The following Examples serve to illustrate the invention.

EXAMPLE 1

Preparation of 5(R,S),6(S,R)p-nitrobenzyl3-(Z)-2-acetamidopropenylthio-6-(IR,S-hydroxyethyl)-7-oxo-1-azabicyclo[3.2.0]hept-2-ene-2-carboxylate (i) Preparation of 5(R,S)6(S,R)p-Nitrobenzyl-3(4,6dimethylpyrimidin-2-ylsulphinyl)-6(1(R,S)-p-nitrobenxyloxycarbonyloxyethyl)-7-oxo-1-azabicyclo[3.2.0]hept-2-ene-2-carboxylate

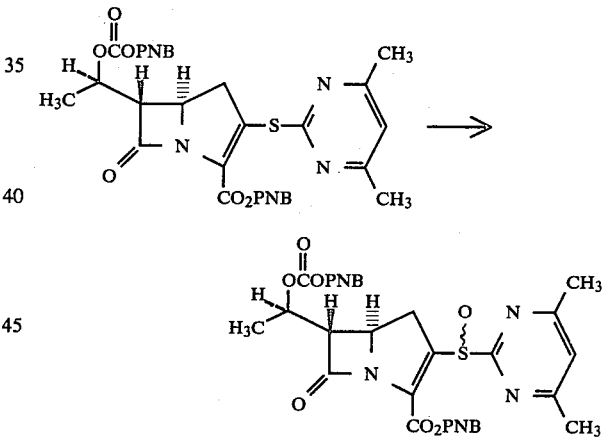

5(R,S),6(S,R) p-Nitrobenzyl-3(4,6dimethyl-pyrimidin-2-yl-thio)-6(1(R,S)-p-nitrobenzyloxycarbonyloxyethyl)-7-oxo-1-azabicyclo[3.2.0]hept-2-ene-2-carboxyulate (0.2 g) was dissolved in dry dichloromethane (20 ml) and treated with m-chloroperbenzoic acid (0.13 g; 1.3 equivs) at ,0° C. The solution was allowed to warm to room temperature during 1 hour and washed with 3% sodium bicarbonate solution (3×10 ml). The organic phase was dried (MgSO$_4$), the solvent evaporated and the residue chromatographed on Merck Kieselgel 60 (<230 mesh) to provide the title compound (0.126 g; 62%) as a gum (3:2 mixture of isomers) ν max (CHCL$_3$) 1785, 1730, 1585, 1520, 1345 cms$^{-1}$. λ max (EtOH) 262 nm. δ(CDCl$_3$) major isomer: 1.44(3H,d,J7 Hz,CH$_3$)1.56(6H,S,2×CH$_3$)2.94(1H,dd,J18,10 Hz, C4—H$_a$) 3.40(1H,dd,J18,8 Hz, C4—H$_b$)3.56(1H,dd,J6.5,3 Hz, C6—H)4.26(1H,ddd, J10,8,3 Hz,C5—H) 5.1 to 5.6 (5H, complex pattern, ×CH₂ and C̲H̲—O 7.12(1H,S,pyrimidinyl-H) 7.54, .64 and 8.2̲3̲ (8H,m's,Ar NO₂'s) minor isomer: 1.46(3H,d,H7 Hz,CH₃)1.54(6H,S,2×CH₃)2.86(1H,dd, J18,8 Hz,C4—H$_a$)3.41(1H,dd,J7,3 Hz,C6—H)3.65(1H,dd,J18,10 Hz, C4—$^H{}_b$)4.38(1H,ddd,J10,8,3 Hz,C5—H) 5.1 to 5.6 (5H, complex pattern, 2×CH₂ and C̲H̲—O)7.12(1H,S, pyrimidinyl-H)7.54, 7.64 and 8.23(8H̲,m's,ArNO₂'s).

(ii) Preparation of 5(R,S),6(S,R)p-nitrobenzyl3-(Z)-2-acetamido-propenylthio-6-(1R,S-hydroxyethyl-7-oxo-1-azabicyclo[3.2.0]hept-2-ene-2-carboxylate

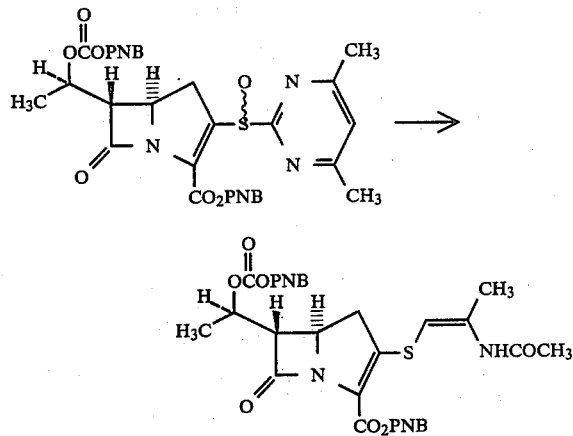

The sulphoxide (0.025 g) was dissolved in dry dimethylformamide (10 ml) and treated with crude sodium 2-acetamidopropenyl thiolate (0.010 g; 1.3 equivs) in dimethylformamide (2 ml) at −50° C. The reaction was stirred at −50° C. for 40 minutes and ethyl acetate (15 ml) and 3% sodium bicarbonate solution (10 ml) were added. The extract was washed twice with 3% sodium bicarbonate solution (15 ml) and dried (MgSO₄). The solvent was evaporated and the residue chromatographed on Merck Kieselgel 60 (<230 mesh) to provide the title compound (0.017 g; 70%) as a gum ν max (CHCl₃) 3370, 1780, 1730, 1705 c,⁻¹. λ max (EtOH) 327, 263 nm. δ(CDCl₃) 1.49(3H,d,J6.5 Hz CH₃) 2.12(3H,S,COCH₃)2.37(3H,S,-=<$_{CH_3}$)2.97(1H,dd,J18,8 Hz,C4—H$_a$) 3.21(1H,dd,H18,9.5 Hz,C4—Hb)3.39(1H,dd,J8,3 Hz,C6—H)4.21(1H,m, C5—H)5.12(1H,brs,C̲H̲=)5.18(1H,m-CH—O)5.28(2H,S,C̲H̲₂) 5.40(2H, ABq, J13Hz,C̲H̲₂)7.56 and 7.67, 8.24 and 8.25 (8H,2×ABq,J7.5 Hz,ArNO₂'s)

EXAMPLE 2

Preparation of p-Nitrobenzyl(5RS,6SR)-3-[(Z)-2-Acetamidoethenyl-thio]-6-[(1RS)-1-p-nitrobenzyloxycarbonyloxyethyl]-7-oxo-1-azabicyclo[3.2.0]hept-2-ene-2-carboxylate

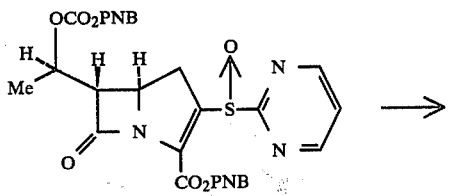

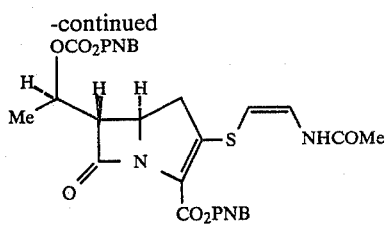

p-Nitrobenzyl(5RS,6SR)-6-[(1RS)-1-p-nitrobenzyloxycarbonyloxyethyl]-3-(2-pyrimidylsulphinyl)-7-oxo-1-azabicyclo[3.2.0]hept-2-ene-2-carboxylate (230 mg) in dichloromethane (25 ml) was treated with benzyldimethyl-n-hexadecylammonium chloride (12 mg), cooled in an ice-bath, and treated with sodium Z-2-acetamidoethenylthiolate (contanimated by 1 molar equivalent NaCl) (77 mg) in water (25 ml). After stirring vigorously for 25 min. the layers were separated, and the dichloromethane layer was washed with dilute aqueous NaHCO₃, followed by brine. After drying (MgSO₄) the solution was evaporated in vacuo and the residue was chromatographed on silica gel (230–400 mesh ASTM), eluting with ethyl acetate to give the title compound (118 mg, 52% yield).

EXAMPLE 3

Preparation of 5(R,S),6(S,R)p-nitrobenzyl-3(pyrimidin-2-sulphinyl)-6(1(R,S)-p-nitrobenzyloxycarbonyloxyethyl)-7-oxo-1-azabicyclo[3.2.0.]hept-2-ene-2-carboxylate

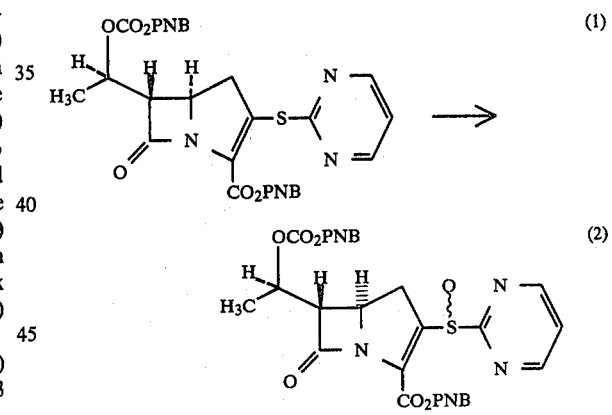

5(R,S),6(S,R)p-nitrobenzyl-3(pyrimidin-2ylthio)-6-(1(R,S)-p-nitrobenzyloxycarbonyloxyethyl)-7-oxo-1-azabicyclo[3.2.0.]hept-2-ene-2-carboxylate (0.093 g) was dissolved in dry dichloromethane (100 ml) and treated with a solution of m-chloroperbenzoic acid (0.022 g) in dichloromethane at 0° C. The solution was stirred for 3 hours and allowed to warm to room temperature. The resulting colourless solution was washed three times with saturated sodium bicarbonate solution, dried over anhydrous magnesium sulphate and concentrated under reduced pressure. The crude product was chromatographed on Merck Kieselgel 60 (<230 mesh) using ethyl acetate as eluant to afford a white foam (0.050 g, 53%) containing the sulphoxide as a 2:3 ratio of isomers.

λ$_{max}$ (EtOH) 264 nm; ν$_{max}$ (CHCl₃) 1800, 1740, 1520 and 1350 cm⁻¹; δ (ppm, CDCl₃) major isomer: 1.45 (3H, d,J=7.5 Hz, —CH₃); 2.91 (1H,dd,J=19, 10 Hz, C₄—H); 3.40 (1H, dd,J=19,10 Hz, C₄—H); 3.57

(1H,dd,J=3.5, 6 Hz, C$_6$—H); 4.26 (1H,ddd,J=3.5,10,10 Hz, C$_5$—H); 5.15 (1H, m, C$_8$—H); 5.23 (2H, s, CH$_2$—Ar); 5.44 (2H, ABq, J=15 Hz, CH$_2$—Ar); 7.53–7.47 (3H, m, Ar—H and pyrimidine-H); 7.67–7.61 (2H, m, Ar—H); 8.26–8.20 (4H, m, Ar—H); 8.89 (2H, d, J=5 Hz, pyrimidine-H) minor isomer: 1.45 (3H d, J=7.5 Hz, —CH$_3$); 2.78 (1H,dd,J=18, 9 Hz, C$_4$—H); 3.42 (1H,dd,J=3.5, 6 Hz, C$_6$—H); 3.66 (1H,dd,J=18, 9 Hz, C$_4$—H); 4.41 (1H,ddd,J=3.5 9,9 Hz, C$_5$—H); 5.15 (1H, m, C$_8$—H); 5.23 (2H, S, CH$_2$—Ar); 5.42 (2H, ABq, J=15 Hz, CH$_2$—Ar); 7.47–7.53 (3H, m, Ar—H and pyrimidine -H); 7.61–7.67 (2H, m, Ar—H); 8.20–8.26 (4H, m Ar—H).

EXAMPLE 4

Preparation of 5(R,S),6(S,R)p-nitrobenzyl-3(4-amino pyrimidin-2-ylthio)-6(1(R,S)p-nitrobenzyloxycarbonyloxyethyl)-7-oxo-1-azabicyclo[3.2.0]hept-2-ene-2-carboxylate

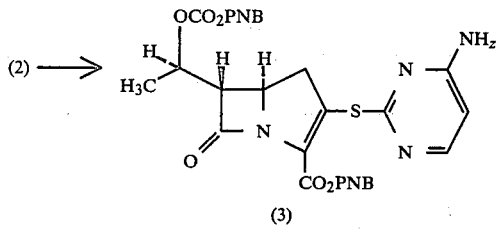

The sulphoxide (2) (0.015 g, as a mixture of isomers) was dissolved in dimethylformamide, cooled to —40° C. and treated with a solution of sodium-2-thiocytosine (0.005 g) in dimethylformamide and stirred for 40 minutes. The resultant solution was poured into excess ethyl acetate and washed five times with 3% sodium bicarbonate solution. The organic phase was dried over anhydrous magnesium sulphate, evaporated under reduced pressure and the residue chromatographed on Merck Kieselgel 60 (<230 mesh) using petrol (bp 60°–80°)/ethyl acetate as eluant to give the desired compound as a colourless oil (0.004 g, 27%), which could be crystallised from ethyl acetate to afford a white crystalline solid.

$\lambda_{max}$ (EtOH) 321 nm; $\nu_{max}$ (CHCl$_3$) 3510, 3400, 1780, 1730 1610, 1520, 1350 cm$^1$; δ (ppm, CDCl$_3$): 1.49 (3H, d, J=7 Hz, CH$_3$); 3.22 (1H, dd, J=9, 18 Hz, C$_4$—H); 3.42 (1H, dd, J=3, 7 Hz, C$_6$—H); 3.81 (1H, dd, J=10, 18 Hz, C$_4$'—H); 4.27 (1H, ddd, J=3, 9, 9 Hz, C$_5$—H; 5.02 (2H, brs, —NH$_2$); 5.18 (1H, m, C$_8$—H); 5.26 (2H, S, CH$_2$—Ar); 5.40 (2H, ABq , J=14 Hz, CH$_2$Ar); 6.23 (1H, d, J=5 Hz, pyrimidine-H); 8.07 (1H, d, J=5 Hz, pyrimidine-H); 7.54 and 8.21 or 8.22 (4H, ABq, J=8.5 Hz, Ar—H); 7.63 and 8.21 or 8.22 (4H, ABq, J=8.5 Hz, Ar—H.

EXAMPLE 5

5(R,S),6(S,R)p-nitrobenzyl-3-(4-pyridylthio)-6(1(R,S)p-nitrobenzyloxycarbonyloxyethyl)-7oxo-1-azabicyclo[3.2.0]hept-2-ene-1-carboxylate

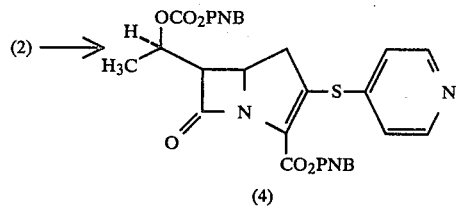

The sulphoxide (2; 0.020 g) was treated with sodium 4-pyridyl thiolate (0.006 g) following the procedure described in example 4. The title product (4) was obtained as a pale yellow oil (0.008 g, 41%).

$\nu_{max}$ (CHCl$_3$) 1790, 1740, 1610, 1520, 1350 cm$^{-1}$. δ (ppm, CDCl$_3$): 1.49 (3H, d, J=6.5 Hz, CH$_3$); 2.82 (1H, dd, J=9, 18 Hz, C$_4$—H); 2.83 (1H, dd, J=9, 18 Hz, C$_4$'—H); 3.35 (1H, dd, J=3, 7.5 Hz C$_6$—H); 4.18 (1H, ddd, J=3, 9, 9 Hz C$_5$—H); 5.14 (1H, dq, J=6.5, 7.5 Hz, C$_8$—H); 5.23 (2H, d, J=5 Hz, CH$_2$—Ar); 5.41 (2H, ABq, J=15 Hz CH$_2$Ar); 7.41 and 8.65 (4H, ABq, pyridyl-H); 7.51 and 8.21 or 8.24 (4H, ABq, J=8.51 Hz, Ar—H); 7.67 and 8.21 or 8.24 (4H, J=8.5 Hz ABq, Ar—H).

EXAMPLE 6

5(R,S),6(S,R)p-nitrobenzyl-3-(5-phenyl-1,2,4-triazin-3-ylthio)-6(1(R,S)p-nitrobenzyloxycarbonyloxyethyl)-7-oxo-1-azabicyclo[3.2.0.]hept-2-ene-2-carboxylate

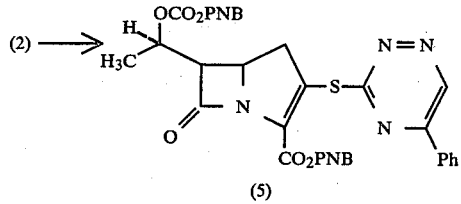

(i) 5-Phenyl-1,2,4-triazine-3thione was prepared according to the literature method (G. Werber et al, J. Heterocyclic Chem., 1977, 14, 1433). A solution of sodium in ethanol was treated with one equivalent of thione and the mixture stirred until all the solid had dissolved. Evaporation of the solvent followed by azeotroping twice with toluene gave the desired sodium thiolate in quantitative yield as an orange solid.

(ii) The sulphoxide (2, 0.020 g) was dissolved in dimethyl formamide, cooled to —40° C. and treated with a solution of sodium-3-thio-5-phenyl-1,2,4-triazine (0.017 g) in dimethylformamide and the mixture stirred for 40 minutes. The resultant solution was poured into excess ethyl acetate and washed five times with 3% sodium bicarbonate solution. The organic phase was dried over anhydrous magnesium sulphate, evaporated under reduced pressure and the residue chromatographed on Merck Kieselgel 60 (<230 mesh) using petrol (b.p. 60°–80°)/ethyl acetate as eluant to give the desired compound (5) as a pale yellow oil (0.008 g, 37%).

$\lambda_{max}$ 325 nm (shoulder), $\nu_{max}$ (CHCl$_3$) 1780, 1730, 1510, 1490, 1350 cm$^{-1}$. δ (ppm, CDCl$_3$): 1.50 (3H), d, J=7.5 Hz, —CH$_3$); 3.29 (1H, dd, J=9, 18 Hz, C$_4$—H); 3.49 (1H, dd, J=3, 8 Hz, C$_6$—H); 3.89 (1H, dd, J=10, 18 Hz, C$_4'$—H); 4.39 (1H, ddd, J=3, 9, 9 Hz, C$_5$—H; 5.16–5.28 (1H, m, C$_8$—H); 5.26 (2H, s, CH$_2$—Ar); 5.33 and 5.56 (2H, ABq, J=15 Hz, CH$_2$—Ar); 7.54 and 8.21 or 8.22 (4H, ABq, Ar—H); 7.65 and 8.21 or 8.22 (4H, ABq, Ar—H); 9.46 (1H, s, triazine-H).

EXAMPLE 7

5(R,S),6(S,R)p-nitrobenzyl-3(4,6-dimethoxy-1,3,5-triazin-2-ylthio)-6(1(R,S)p-nitrobenzyloxycarbonyloxyethyl)-7-oxo-1-azabicyclo[3.2.0]hept-2-ene-2-carboxylate

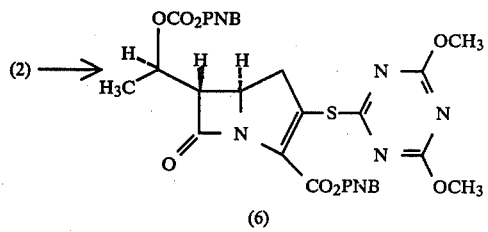

(6)

(i) 2-Thio-4,6-dimethoxy-1,3,5 triazine has prepared according to the literature (O. Diels and M. Liebermann, Chem. Br., 1903, 36, 3191). A solution of sodium in ethanol was treated with one equivalent of thiol and the mixture stirred until all the solid had dissolved. Evaporation of the solvent followed by azeotroping twice with toluene gave the desired sodium thiolate in quantitative yield as a white crystalline solid.

(ii) The sulphoxide (2, 0.040 g) was treated with sodium-2-thio-4,6-dimethoxy-1,3,5-triazine (0.015 g) using the procedure described in example 6. The title compound was obtained, after work-up, as a pale yellow gum (0.0009 g, 22%). $\lambda_{max}$ 262, 315 (shoulder)nm. $\nu_{max}$ (CHCl$_3$) 1780, 1730, 1520, 1480, 1350 cm$^{-1}$. δ (ppm, CDCl$_3$): 1.49 (3H, d, J=7.5 Hz, —CH$_3$); 3.23 (1H, dd, J=9, 19 Hz, C$_4$—H); (1H, dd, J=2.5 8 Hz, C$_6$—H); 3.95 (1H, dd, J=10, 19 Hz, C$_4'$—H); 4.03 (6H, S, —OCH$_3$); 4.64 (1H, ddd, J=9, 9, 2.5 Hz, C$_5$—H), 5.19 (1H, dq, J=7.5, 8 Hz, C$_8$—H); 5.27 (2H, S, CH$_2$Ar); 5.39 (2H, ABq, J=15 Hz, CH$_2$—Ar); 7.55 and 8.21 or 8.22 (4H, ABq, Ar—H); 7.63 and 8.21 or 8.22 (4H, ABq, Ar—H).

EXAMPLE 8

5(R,S), 6(S,R) p-nitrobenzyl-3 (4,6-diamino pyrimidin-2-yl thio)-6-(1(R,S) p-nitrobenzyloxycarbonyloxyethyl)-7-oxo-1-azabicyclo[3.2.0.]hept-2-ene-2-carboxylate

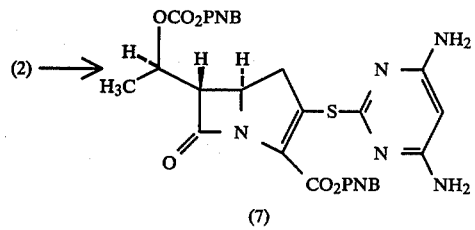

(7)

The sulphoxide (2, 0.030 g) was treated with the sodium salt of 4,6-diamino-2-mercapto pyrimidine (0.010 g) following the procedure described in example 4. The title product (7) was obtained as a colourless oil (0.007 g, 23%). $\lambda_{max}$ 325 nm, $\nu_{max}$ (CHCl$_3$) 3520, 3420, 1785, 1725, 1620, 1525, 1350 cm$^{-1}$. δ (ppm, CDCl$_3$): 1.49 (3H, d, J=7.5 Hz, C$_8$—CH$_3$); 3.22 (1H, dd, J=9, 18 Hz, C$_4'$—H); 3.40 (1H, dd, J=3, 8 Hz, C$_6$—H); 3.78 (1H, dd, J=9, 18 Hz, C$_4$—H); 4.23 (1H, ddd, J=3, 9, 9 Hz, C$_5$—H); 5.16 (1H, dq, J=7.5, 8 Hz, C$_8$—H); 5.25 (2H, S, CH$_2$Ar); 5.30 and 5.49 (2H, ABq, J=14 Hz, CH$_2$—Ar); 5.34 (1H, S, pyrimidine-H); 7.54 and 8.23 or 8.21 (4H, ABq, J=8.5 Hz, Ar—H); 7.64 and 8.23 or 8.21 (4H, ABq, J=8.5 Hz, Ar—H).

EXAMPLE 9

5(R,S), 6(S,R) p-nitrobenzyl-3-(1-methyl tetrazol-5-yl thio)-6(1(R,S) p-nitrobenzyloxycarbonyloxyethyl)-7-oxo-1-azabicyclo[3.2.0.]hept-2-ene-carboxylate

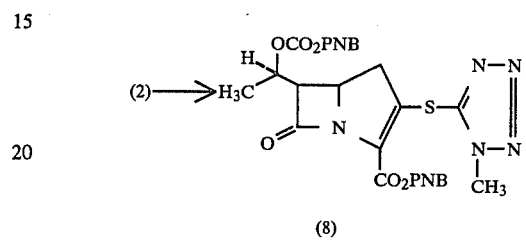

(8)

The sulphoxide (2; 0.020 g) was dissolved in dry dimethylformamide and treated with triethylamine (2 drops) at −50° C., followed by 1-methyl-5-thio tetrazole (0.005 g). The mixture was allowed to warm to room temperature and stirred for 8 hours. The resultant solution was poured into excess ethyl acetate and washed five times with 3% aqueous sodium bicarbonate. The organic phase was dried over anhydrous magnesium sulphate, evaporated under reduced pressure and the residue chromatographed on Merck Kieselgel 60 (<230 mesh) using petrol (b.p. 60°–80° C.)/ethyl acetate as eluant, to give the title compound (8) as a colourless oil (0.0035 g, 18%). $\lambda_{max}$ 265, 305 (shoulder)nm., $\nu_{max}$ 1795, 1740, 1520, 1350 cm$^{-1}$. δ (ppm, CDCl$_3$): 1.46 (3H, d, J=6.5 Hz, C$_8$—CH$_3$); 3.05 (1H, dd, J=9, 18 Hz, C$_4$—H); 3.28 (1H, dd, J=9, 18 Hz, C$_4'$—H); 3.43 (1H, dd, J=3, 7.5 Hz, C$_6$—H); 4.10 (3H, S, N—CH$_3$); 4.29 (1H, ddd, J=3, 9, 9 Hz, C$_5$—H); 5.15 (1H, dq, J=6.5, 7.5 Hz, C$_8$—H); 5.24 (2H, S, CH$_2$—Ar); 5.34 and 5.65 (2H, ABq, J=14 Hz, CH$_2$—Ar); 7.55 and 8.24 or 8.25 (4H, ABq, J=8.5 Hz, Ar—H); 7.65 and 8.24 or 8.25 (4H, ABq, J=8.5 Hz, Ar—H).

EXAMPLE 10

5(R,S), 6(S,R) p-nitrobenzyl-3(Z-2-acetamido-1-ethenyl thio)-6(1(R,S) p-nitrobenzyloxycarbonyloxyethyl)-7-oxo-1-azabicyclo[3.2.0.]hept-2-ene-2-carboxylate

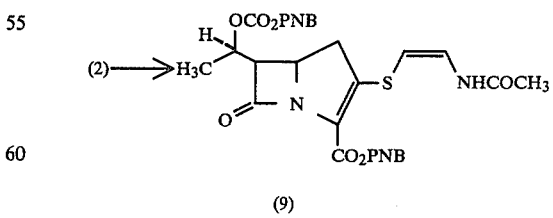

(9)

The sulphoxide (2; 0.020 g was dissolved in methylene chloride (2 ml) and cooled in an ice bath water (1 ml) and sodium Z-2-acetamido-1-ethenyl thiolate (0.006 g, 1.3 eq) were added, followed by cetyl triethyl ammonium chloride (1 drop). The reaction was stirred vigorously at 0° C. for 5 minutes. The resulting mixture was diluted with methylene chloride, separated, and the organic layer washed twice with 3% sodium bicarbonate solution. The solvent was evaporated and the residue chromatographed on Kieselgel 60 (<230 mesh) using petrol (b.p. 60°14 80°)/ethyl acetate as eluant, to afford the title compound (9) as a pale yellow oil (0.004 g, 20%). $\lambda_{max}$ (EtOH) 326 nm, $\nu_{max}$ 1785, 1750, 1700, 1630, 1610, 1525, 1350 cm$^{-1}$.

EXAMPLE 11

5(R,S), 6(S,R) p-nitrobenzyl-3(1-methyl tetrazol-5-yl thio)-6(1(R,S) p-nitrobenzyloxycarbonyloxyethyl)-7-oxo-1-azabicyclo[3.2.0.]hept-2-ene-2-carboxylate

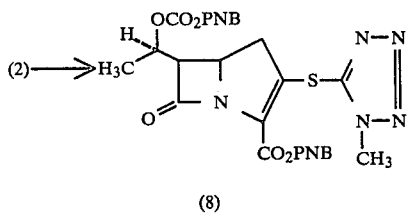

(8)

The sulphoxide (2; 0.020 g) was treated with the sodium salt of 1-methyl, 5-thio tetrazole (0.006 g) under the phase transfer catalysis conditions described in example 10. In this instance it was necessary to carry out the reaction at room temperature for 48 hours. The title compound was obtained, after work-up, as a pale yellow oil (0.004 g, 20%).

$\lambda_{max}$ 265, 305 (shoulder) nm.

EXAMPLE 12

5(R,S), 6(S,R)-3(4-aminopyrimidin-2-yl thio)-6(1(R,S)-hydroxyethyl)-7-oxo-1-azabicyclo[3.2.0.]hept-2-ene-2-carboxylate

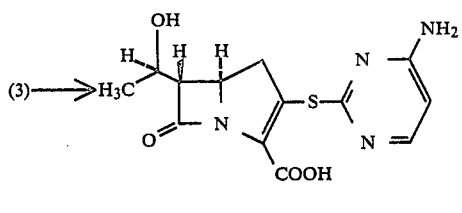

(10)

The product from example 4 (3; 0.020 g) was dissolved in 20% aqueous dioxan (20 ml) containing pH7 phosphate buffer (M/20, 2 ml) and 10% Pd/C (prehydrogenated, 0.020 g) and was hydrogenated at ambient temperature and pressure for two hours. The resultant solution was diluted with water (5 ml), filtered through Kieselguhr, the organic solvent evaporated and the aqueous solution extracted with ether (3×10 ml). Examination of the aqueous phase by UV showed it to contain the title compound (10) (0.007 g, 70%).

$\lambda_{max}$ (H$_2$O) 300 nm.

EXAMPLE 31

Sodium 5(R,S), 6(S,R)-3(1-methyl tetrazol-5-yl thio)-6-(1(R,S)-hydroxyethyl)-7-oxo-1-azabicyclo[3.2.0.]hept-2-ene-2-carboxylate

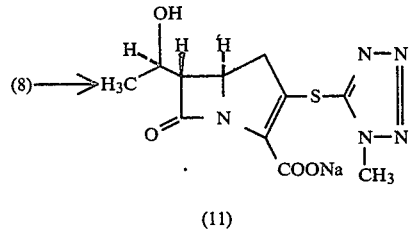

(11)

The product from example 9 (8; 0.007 g) was hydrogenated under the conditions described in example 12. The resulting solution from the hydrogenation was diluted with water (2 ml), filtered through kieselguhr, and treated with an aqueous solution of sodium bicarbonate (0.0015 g). The organic solvent was evaporated and the aqueous solution washed with ethyl acetate (3×5 ml). Examination of the aqueous phase by UV showed the presence of the title product (11) (0.00075 g, 20%).

$\lambda_{max}$ (H$_2$O) 285 nm.

EXAMPLE 14

5(R,S), 6(S,R)-3(4,6-dimethoxy-1,3,5-triazin-2 yl thio)-6-(1(R,S)-hydroxyethyl)-7-oxo-1-azabicyclo[3.2.0]hept-2-ene-2-carboxylate

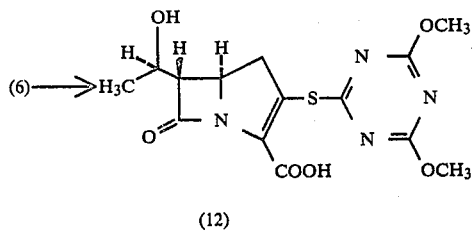

(12)

The product from example 7 (6; 0.004 g) was dissolved in 20% aqueous dioxan (5 ml) containing pH7 phosphate buffer (M/20, 0.5 ml) and 10% Pd/c (prehydrogenated, 0.004 g) and was hydrogenated at ambient temperature and pressure for two hours. The resultant solution was diluted with water (1 ml), filtered through kieselguhr, the organic solvent evaporated and the aqueous solution extracted with ether (3×5 ml). Examination of the aqueous phase by UV showed it to contain the title compound (12) (0.0014 g, 47%).

$\lambda_{max}$ (H$_2$O) 289 nm.

EXAMPLE 15

5(R,S), 6(S,R)-3(5-phenyl-1,2,4-triazin-3-yl thio)-6(1(R,S)-hydroxyethyl)-7-oxo-1-azabicyclo[3.2.0.-]hept-2-ene-2-carboxylate

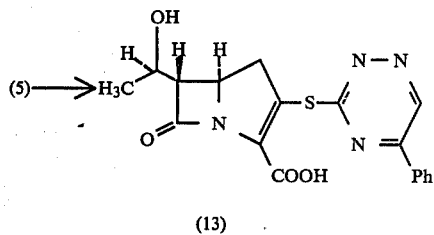

(13)

The product from example 6 (5: 0.006 g) was hydrogenated under the conditions described in example 12. After work-up the title compound (13) was obtained in aqueous solution (0.0005 g, 13%).

$\lambda_{max}$ (H$_2$O) 287 nm.

EXAMPLE 16 p-Nitrobenzyl 3-(2-carbamoylethyl thio)-7-oxo-1-azabicyclo[3.2.0.]hept-2-ene-2-carboxylate

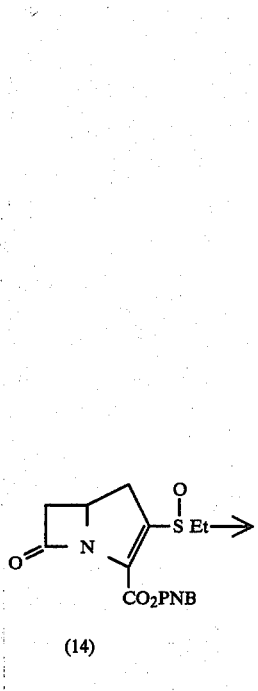

p-Nitrobenzyl 2-ethylsulphinyl-7-oxo-1-azabicyclo[3.2.0.]hept-2-ene-2-carboxylate (14), (50 mg; 0.137 m moles) in anhydrous dimethylformamide (DMF) (5 cm$^3$) was cooled, with stirring, to −50° C. 3-Mercapto-propionamide (15 mg., 0.143 m moles) in anhydrous DMF (2 cm$^3$) was added, followed by anhydrous triethylamine (16.6 mg., 0.164 m moles). The reaction mixture was maintained at −50° C. for a further 30 min. and then allowed to warm to room temperature. Dilution with ethyl acetate (15 cm$^3$) followed by washing with brine (2×20 cm$^3$) and water (20 cm$^3$) afforded a crystalline precipitate which was filtered off and dried. The organic phase was dried and solvent removed in vacuo to give a solid after trituration with ethyl acetate. Total yield of product (15), 21 mg (39%). Recrystallised from ethanol, m.p. 145° C.-146° C. $\nu_{max}$ (Mull) 3375, 3180, 1800, 1700 and 1650 cm$^{-1}$, $\delta$ ppm (d6-DMSO) 2.40 (2H, t, J 7.2 Hz., —CO.CH$_2$—), 2.99-3.10 (2H, m, 2C4—H partially masked by $\overline{d}$ of C6—$\beta$H), 3.10 (1H, dd, J 2.7, 16.4 Hz., C6—$\beta$H), 3.19-3.38 (2H, m, —SCH$_2$-partially masked by H$_2$O signal), 3.46 (1H, dd, J 5.4, 16.6 Hz., C6—$\alpha$H), 4.17 (1H, m, C5—H), 5.28 and 5.41 (2H, ABq J 14.1 Hz., —CH$_2$Ph), 6.95 and 7.40 (2H, broad s, exchangeable —N$\overline{H_2}$), 7.68 and 8.23 (4H, d, J 8.9 Hz, phenyl H). Found: 349.0726, C$_{15}$H$_{15}$N$_3$O$_6$S requires 349.0732, Found: C, 52.22; H, 4.59; N, 10.36; S, 8.15: C$_{17}$H$_{17}$N$_3$O$_6$S requires C, 52.17; H, 4.38; N, 10.74; S, 8.19%.

EXAMPLE 17

Sodium 5RS, 6SR-3-(Z-2-acetamidoethenylthiol)-6-hydroxyisopropyl-7-oxo-1-azabicyclo[3.2.0.]hept-2-ene-2-carboxylate

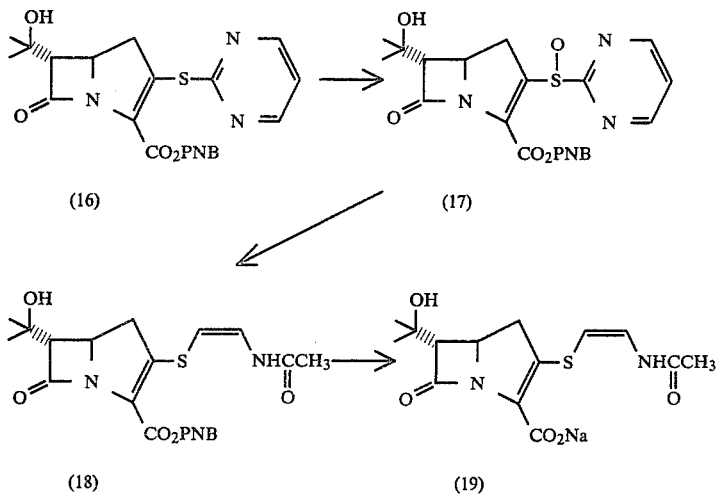

The ester (16) (200 mg, 0.44 m mmol) in solution in dry dichloromethane (20 cm$^3$) was treated with a solution of m-chloroperbenzoic acid [1.2 equivs] in dichloromethane at 0° C. After stirring for 3 hours at room temperature, the solution was washed several times with sodium bicarbonate solution, then dried over sodium sulphate, filtered and evaporated. Chromatography of the crude product on silicagel, eluting with ethyl acetate:acetone in the ratio of 1:1, yielded the sulphoxide (17) (78 mg 38%).

$\nu_{max}$ (CHCl$_3$): −1785, 1730, 1520, 1320 cm$^{-1}$.

A solution of the sulphoxide (17) (78 mg 0.16 mmole) in dry DMF (25 cm$^3$) at −50° C. was treated with a solution of sodium —Z-2-acetamido-1-ethenyl thiolate [1.3 equivs] in dry DMF. The resultant yellow solution was stirred at −50° C. for 40 minutes then poured into excess ethyl acetate (30 cm$^3$) and washed 5 times with 3% sodium bicarbonate solution. The organic layer was dried over sodium sulphate, filtered and evaporated. Chromatography on silicagel 60 eluting with ethylacetate:acetone 1:1 yielded (18) [22 mg 29%] $\nu_{max}$(CHCl$_3$): —1780, 1700, 1630, 1525, 1460, 1330 cm$^{-1}$.

A solution of (18) [22 mg, 0.05 mmol] in aqueous dioxan (20 cm$^3$) was added to prehydrogenated 10% Pd/C catalyst [46 mg]. After hydrogenation at room temperature and pressure for 2 hours sodium bicarbonate solution (1 equiv.) was added. The solution was filtered through Celite, washed with water, and the dioxane removed in vacuo. The aqueous residue was extracted with ether and the sodium salt was purified by chromatography on HP20 using water as eluent to yield (19) [4.8 mg, 29%].

$\lambda_{max}$ (H$_2$O): 309, 229 nm.

EXAMPLE 18 p-Nitrobenzyl (5R,6S)-3-phenylthio-6[(S)-1-hydroxyethyl]-7-oxo-1-azabicyclo[3.2.0.]hept-2-ene-2-carboxylate

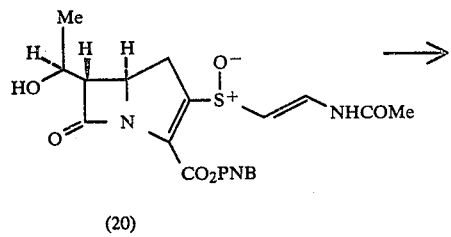

A solution of the sulphoxide (20) (150 mg) in DMF (20 ml) was cooled to −50°. Triethylamine (65 mg) was added with stirring followed by thiophenol (43 μl). Stirring was continued at −50° for 10 minutes. The solution was poured into ethyl acetate (150 ml) and the organic solution was washed with pH 7 buffer solution (150 ml) and dilute brine (3×150 ml) before drying with MgSO$_4$. The solution was concentrated in vacuo and the residue chromatographed on a column of silica gel using a gradient elution of 50% petrol-ethyl acetate to 10%. The desired product was crystallised from ethyl acetate-petrol to afford crystals of the title compound; (21) (30 mg) m.p. 160°-162°; $\lambda_{max}$ (EtOH) 318 (15,535) and 265 nm (12,785); $\nu_{max}$(CH$_2$Cl$_2$) 3590, 1780 and 1705 cm$^{-1}$; δ (CDCl$_3$) 1.30 (3H, d, J 6 Hz, MeCH), 1.88 (1H, d, J 5 Hz, OH), 2.66 (2H, d, J 9 Hz, 4—CH$_2$), 3.17 (1H, dd, J ca 3 and 5 Hz, 6—CH), 3.90-4.25 (2H, m, 5—CH and CHMe), 5.25 and 5.56 (each 1H, d, J 13 Hz, CH$_2$Ar) 7.30-7.70 (5H, m, Ph) and 7.65 and 8.22 (each 2H, d, J 9 Hz, ArCH$_2$) [M+, 440.1063, C$_{22}$H$_{20}$N$_2$O$_6$S requires 440.104].

EXAMPLE 19 p-Nitrobenzyl (5R,6S)-6-[(S)-1-hydroxyethyl]-3-(2-pyrimidylthio)-7-oxo-1-azabicyclo[3.2.0.]hept-2-ene-2-carboxylate

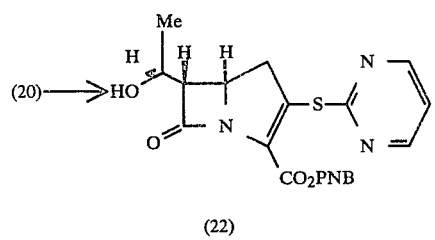

The sulphoxide (20) (200 mg) was dissolved in DMF (20 ml) and the solution was cooled to −35°. Lithium 2-pyrimidylthiolate (56 mg) was added and the solution was stirred at −35° for 40 min. Ethyl acetate (100 ml) was added and the solution was washed with pH 7 buffer solution (100 ml) water (3×100 ml) and brine (50 ml). Evaporation of the dried (MgSO$_4$) organic solution gave a residue which was chromatographed on silica gel using ethyl acetate to eluate. Fractions containing the desired product were combined and evaporated to afford a white solid (85 mg). Crystals of the title compound (22) were obtained from ethyl acetate-ether; m.p. 158°-160°, [α]$_D^{20}$ (C. 0.5, DMF) +56°, $\lambda_{max}$ (EtOH) 320 (14,190) and 262 nm (14,390), $\nu_{max}$ (KBr) 1775 and 1690 cm$^{-1}$; δ (CDCl$_3$) 1.40 (3H, d, J 6.5 Hz, MeCH), 1.88 (3H, br s, OH), 3.24 (2H, dd, J 18 and 9 Hz, 4—CHa), 3.36 (1H, dd, J 3 and 5.5 Hz, 6—CH), 3.82 (1H, dd, J 18 and 9 Hz, 4—CH$_b$), 4.18-4.32 (2H, m, 5—CH and CHMe), 5.29 and 5.51 (each 2H, d, J 13.5 Hz, CH$_2$Ar), 7.11 (1H, t, J 4.5 Hz, pyrimidyl 5—CH), 7.66 and 8.22 (2H, d, J 9 Hz, ArCH$_2$) and 8.58 (2H, d, J 4.5 Hz, pyrimidyl 6—CH and 4—CH); [Found: C, 54.14; H, 4.16; N, 12.53%; M+, 442.0928. C$_{20}$H$_{18}$N$_4$O$_6$S requires C, 54.29; H, 4.10; N, 12.66%; M, 442.0947].

EXAMPLE 20 p-Nitrobenzyl (5R,6R)-6-[(S)-1-hydroxyethyl]-3-(2-pyrimidylthio)-7-oxo-1-azabicyclo[3.2.0]hept-2-ene-2-carboxylate

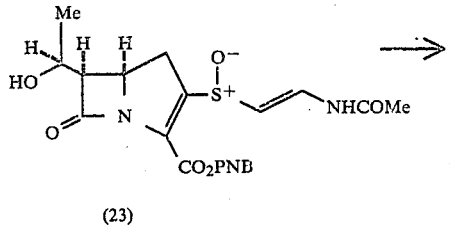

The sulphoxide (23) (480 mg) was converted to the derivative (24) by the process of Example 19. The title ompound (24) was obtained as a foam (220 mg) which afforded white crystals from ethyl acetate-petroleum ether (60°–80°); m.p. 144°–147°; $\lambda_{max}$ (EtOH) 318 (13,925) and 262 nm. (14,305); $\nu_{max}$ (KBr) 1780 and 1700 cm$^{-1}$; δ (CDCl$_3$) 1.43 (3H, d, J 6.5 Hz, MeCH), 2.09 (1H, d, J 5 Hz, OH), 3.52 (1H, dd, J 9 and 18.5 Hz, 4—CH$_a$), 3.64 (1H, dd, $\underline{H}$ 6 and 9 Hz, 6—CH), 3.78 (1H, dd, J 18.5 and 10 HZ, 4—CH$_b$), 4.26 (1H, m, 5—CH), 4.43 (1H, dt, J 6 and 10 Hz, MeCH), 5.29 and 5.51 (each 1H, d, J 13.5 Hz, CH$_2$Ar), 7.12 (1H, t, J 5 Hz, pyrimidyl 5—CH), 7.65 and 8.23 (each 2H, d, J 9 Hz, Ar—CH$_2$), 8.60 (2H, d, J 5 Hz, pyrimidyl 4—CH and 6—CH) [Found: C, 54.05; H, 4.18; N 12.63%; M$^+$, 442.0958; C$_{20}$H$_{18}$N$_4$O$_6$S requires C, 54.29; H, 4.10; N, 12.66%; M, 442.0947].

EXAMPLE 21

Sodium (5R,6S)-6-[(S)-1-hydroxyethyl]-3-(2-pyrimidylthio)-7-oxo-1-azabicyclo[3.2.0]hept-2-ene-2-carboxylate

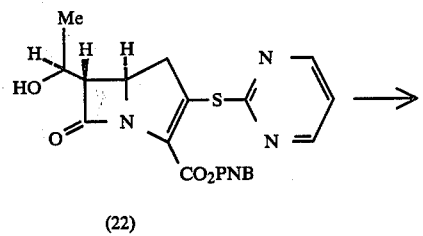

(22)

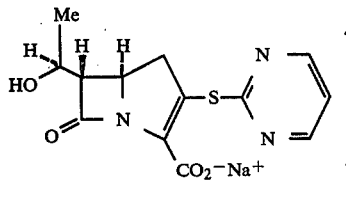

(25)

A solution of the derivative (22) (30 mg) in 30% aqueous dioxan (10 ml) was shaken with hydrogen in the presence of 5% Pd on C (45 mg), which had been prehydrogenated for 0.5 h. After 2 h sodium bicarbonate (5.7 mg) was added and the mixture was filtered through Celite, washing the pad well with water (30 ml). The solution was concentrated in vacuo to ca 30 ml and was then washed (×3) with ethyl acetate (50 ml). The aqueous layer was then concentrated in vacuo to ca 5 ml, and chromatographed on a column (5×2.5 cm) of Biogel P2. Fractions containing the product (identified by $\lambda_{max}$ 296 nm in the uv spectrum) were combined and freeze-dried to afford the title compound (25) (11 mg); $\lambda_{max}$ (H$_2$O) 296 and 246 nm, $\nu_{max}$ (KBr) 1755 1600 and 1560 cm$^{-1}$.

EXAMPLE 22

Sodium (5R,6R)-6-[(S)-1-hydroxyethyl]-3-(2-pyrimidylthio)-7-oxo-1-azabicyclo[3.2.0]hept-2-ene-carboxylate

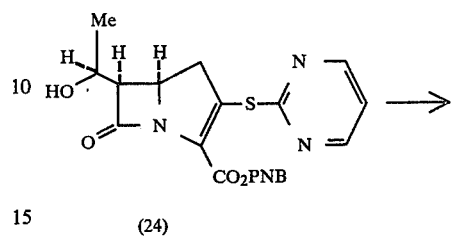

(24)

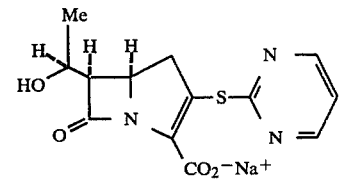

(26)

The derivative (24) (100 mg) was converted into the salt (26) by the method described in Example 21. The title compound (26) was obtained as a freeze-dried solid; $\lambda_{max}$ (H$_2$O) 294 and 245 nm; $\nu_{max}$ (KBr) 1750, 1600 and 1560 cm$^{-1}$.

EXAMPLE 23 p-Nitrobenzyl (5R,6S)-6-[(R)-1-formyloxyethyl]-3-(2-pyrimidylthio)-7-oxo-1-azabicyclo[3.2.0.]hept-2-ene-2-carboxylate

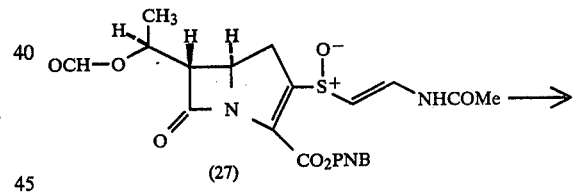

(27)

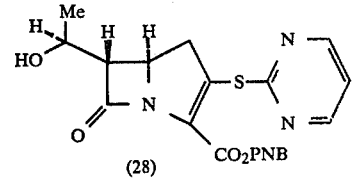

(28)

The O-formyl derivative (27) (260 mg) was treated with sodium 2-pyrimidylthiolate (92 mg) in DMF (30 ml) in the manner described in Example 19. Work-up as described therein, and chromatography on silica gel using 30% petrol-ethyl acetate to elute, afforded the title compound as a foam (62 mg); $\lambda_{max}$ (EtOH) 320 and 263 nm; $\nu_{max}$ (CH$_2$Cl$_2$) 1780 1725 and 1700 sh cm$^{-1}$; δ (CDCl$_3$) 1.45 (3H, d, J 6.5 Hz, MeCH), 3.22 (1H, dd, J 18 and 9 Hz, 4—CH$_a$), 3.45 (1H, dd, J 3 and 7.5 Hz, 6—CH), 3.86 (1H, dd, J 18 and 10 Hz, 4—CH$_b$), 4.31 (1H, ca dt, J 3 and 9.5 Hz, 5—CH), 5.27 and 5.52 (each 1H, d, J 14 Hz, CH$_2$Ar), ca 5.40 (1H, m, C$\underline{H}$CH$_3$), 7.12 (1H, t, J 5 Hz, pyrimidyl 5—CH), 7.65 and 8.21 (each 2H, d, J 9 Hz, ArCH$_2$), 8.07 (1H, s, OCHO) and 8.58

(2H, d, J 5 Hz, pyrimidyl 4—CH and 6—CH) [M+, 470,0876, C₂₁H₁₈N₄O₇S requires 470.0895].

EXAMPLE 24

Sodium (5R,6S)-6-[(R)-1-formyloxyethyl]-3-(2-pyrimidylthio)-7-oxo-1-azabicyclo[3.2.0]hept-2-ene-2-carboxylate

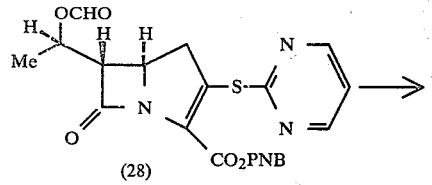

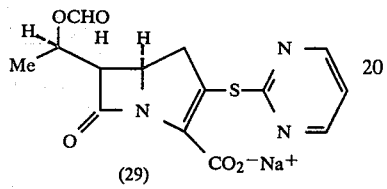

Hydrogenolysis of the ester (28) (15 mg) was performed as described in Example 26. The title salt (e10) was obtained as a freeze-dried solid; λ$_{max}$ (H₂O) 295 and 245 nm; ν$_{max}$ (KBr) 1760, 1720 and 1600 cm⁻¹

EXAMPLE 25 p-Nitrobenzyl (5R,6S)-6-[(R)-1-hydroxyethyl]-3-(2-pyrimidylthio)-7-oxo-1-azabicyclo[3.2.0]hept-2-ene-2-carboxylate

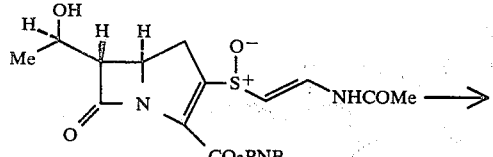

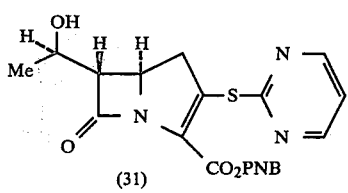

The sulphoxide (30) (62 mg) was converted to derivative (31) by the use of sodium 2-pyrimidylthiolate (24 mg) in DMF (10 ml) in the manner described in Example 19. The title compound (31) was obtained as a white solid (22 mg); λ$_{max}$ (EtOH) 320 (14,295) and 262 (14,295) nm; ν$_{max}$ (KBr) 1775 and 1700 cm⁻¹; δ (CDCl₃) 1.38 (3H, d, J 6.5 Hz, MeCH), 1.87 (1H, br s, OH), 3.25 (1H, dd, J 9 and 18 Hz, 4—CH$_a$), 3.30 (1H, dd, J 3 and 7 Hz, 6—CH), 3.86 (1H, dd, J 10 and 18 Hz, 4—CH$_b$), ca 4.30 (1H, m, CHMe), 4.37 (1H, dt, J 3 and 9.5 Hz, 5—CH), 5.31 and 5.52 (each 1H, d, J 14 Hz, CH₂Ar), 7.13 (1H, t, J 5 Hz, pyrimidyl 5—CH), 7.67 and 8.24 (each 2H, d, J 9 Hz, CH₂Ar) and 8.61 (2H, d, J 5 Hz, pyrimidyl 6—CH and 4—CH) [M+, 422].

EXAMPLE 26

Sodium (5R,6S)-6-[(R)-1-hydroxyethyl]-3-(2-pyrimidylthio)-7-oxo-1-azabicyclo[3.2.0]hept-2-ene-2-carboxylate

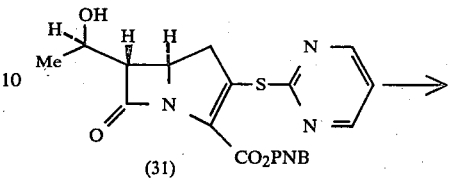

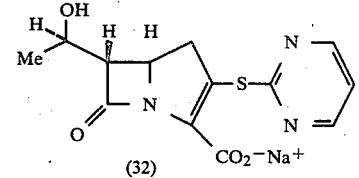

5% Pd-C (100 mg) was shaken with hydrogen with 30% aqueous dioxan (10 ml) for 0.5 hr. A solution of the ester (31) (67 mg) in 30% aqueous dioxan (1 ml) was admitted to the flask and hydrogenation was continued for 2 h. Sodium bicarbonate (13 mg) was added and the solution was filtered through Celite washing with water (30 ml). The solution was concentrated in vacuo to 30 ml and then washed with ethyl acetate (3 × 50 ml). The aqueous solution was further concentrated in vacuo to ca 5 ml and then freeze-dried to afford the title salt (32) as a solid (42 mg); λ$_{max}$ (H₂O) 296 and 246 nm.

EXAMPLE 27 p-Nitrobenzyl (5R,6R)-6-[(S)-1-hydroxyethyl]-3-(1-methylimidazol-2-ylthio)-7-oxo-1-azabicyclo[3.2.0]hept-2-ene-2-carboxylate

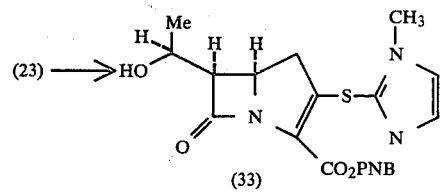

The sulphoxide (23) (380 mg) was dissolved in dichloromethane (50 ml) and sodium 1-methylimidazole-2-thiolate (130 mg) was dissolved in water (10 ml). The two solutions were vigorously stirred together in the presence of tetra-n-butylammonium bromide (53 mg) for 3 min at room temperature. The organic layer was partitioned off and washed with water (2 × 50 ml) and brine (30 ml) before drying (MgSO₄) and evaporating in vacuo. The residue was chromatographed on a column of silica-gel carefully eluting with chloroform followed successively by mixtures of 2.5%, 5%, 7.5% 10% and 15% ethanol in chloroform. The first-eluted component consisted of the title derivative which was obtained as a foam (64 mg). Further chromatography of this product in the same way afforded a pure sample of the title compound (33) (46 mg); λ$_{max}$ (EtOH) 306 and 267 nm; ν$_{max}$ (CHCl₃) 1780 and 1700 cm⁻¹; δ (CDCl₃) 1.36 (3H, d, J 6.5 Hz, MeCH), 2.52 (1H, dd, J 10 and 19 Hz, 4—CH$_a$), 3.17 (1H, dd, J 9 and 19 Hz, 4—CH$_b$), 3.57 (1H, dd, J 5.5 and 8.5 Hz, 6—CH), 3.75 (3H, s, N—Me), 4.15–4.30 (2H, m, 5—CH and MeC$\underline{H}$), 5.30 and 5.54 (each 1H, d, J 13 Hz, C$\underline{H}_2$Ar), 7.08 and 7.17 (each 1H, d, J 1 Hz, imidazole C$\underline{H}$×2), 7.67 and 8.24 (each 2H, d, J 8.5 Hz C$_6\underline{H}_4$NO$_2$).

EXAMPLE 28

Sodium (5R,6R)-6-[(S)-1-hydroxyethyl]-3-(1-methylimidazol-2-ylthio)-7-oxo-1-azabicyclo[3.2.0.]hept-2-ene-2-carboxylate

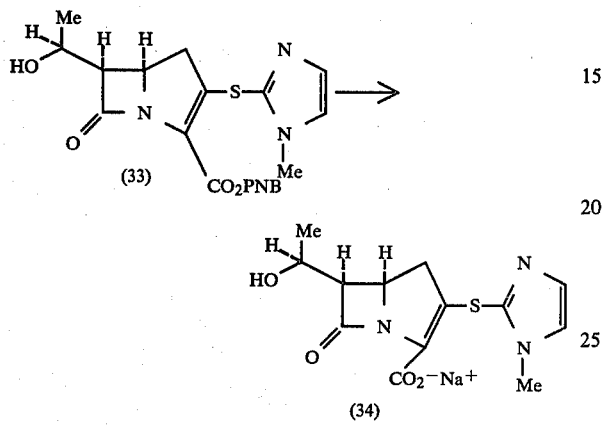

Hydrogenolysis of the ester (33) (30 mg) over 5% Pd-C (45 mg) in 30% aqueous dioxan (10 ml) was performed as described in Example 26. The title salt (34) was obtained as a freeze-dried solid (9 mg); $\lambda_{max}$ (H$_2$O) 291 and 226 nm; $\nu_{max}$ (KBr) 1770, 1665 sh and 1615 cm$^{-1}$.

EXAMPLE 29 p-Nitrobenzyl (5R,6S)-3-[(E)-2-acetamidoethenylsulphinyl]-6-[(S)-1-hydroxyethyl]-7-oxo-1-azabicyclo[3.2.0]hept-2-ene-2-carboxylate

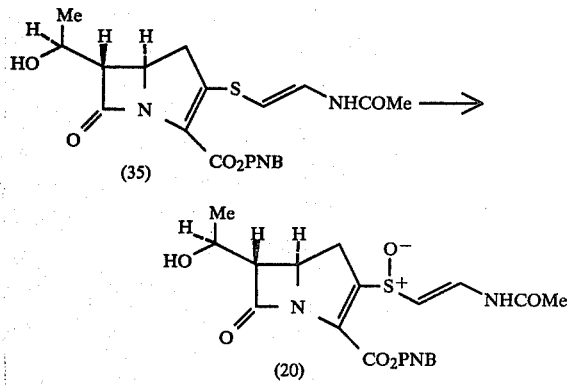

A solution of the ester (35) (500 mg) in 10% ethanol chloroform (50 ml) was cooled to 0° and treated with m-chloroperbenzoic acid (270 mg). After stirring for 0.5 h at 0°, triethylamine (158 mg) was added to the solution which was then concentrated in vacuo to small volume (ca 5 ml). The solution was loaded onto a silica-gel column which was then eluted with chloroform followed by 5%, 10% 15%, 20%, 25% and 30% ethanol in chloroform. Fractions containing the sulphoxide were combined and evaporated in vacuo. The resulting foamy product was triturated with ethyl acetate-ether to afford the title compound (20) as a white solid (375 mg). The product consisted of a mixture of sulphoxide diastereoisomers; $\nu_{max}$ (CH$_2$Cl$_2$) 1785, 1720 and 1630 cm$^{-1}$.

EXAMPLE 30 p-Nitrobenzyl (5R,6R)-3-[(E)-2-acetamidoethenylsulphinyl]-6-[(S)-1-hydroxyethyl]-7-oxo-1-azabicyclo[3.2.0]hept-2-ene-2-carboxylate

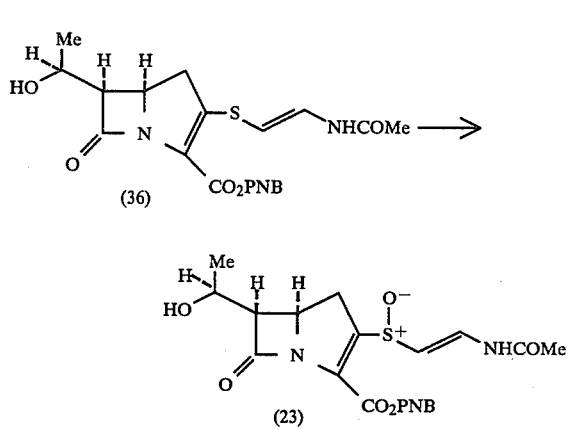

The ester (36) (500 mg) was converted into the title sulphoxide diastereoisomers (23) by the methodology of Example 29.

EXAMPLE 31 p-Nitrobenzyl (5R,6S)-3-[(E)-2-acetamidoethenylsulphinyl]-6-[(R)-1-hydroxyethyl]-7-oxo-1-azabicyclo[3.2.0]hept-2-ene-2-carboxylate

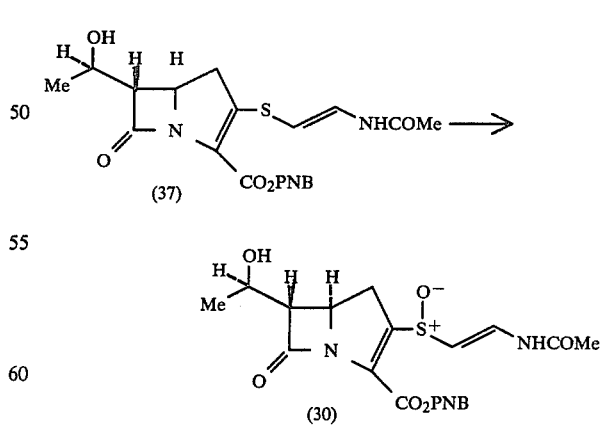

The derivative (37) (64 mg) was treated with m-chloroperbenzoic acid as described in Example 29, to afforded the title sulphoxide diastereoisomers (30) as a foamy solid (62 mg).

EXAMPLE 32 p-Nitrobenzyl (5R,6S)-3-[(E)-2-acetamidoethenylsulphinyl]-6-[(R)-1-formyloxyethyl]-7-oxo-1-azabicyclo[3.2.0]hept-2-ene-2-carboxylate

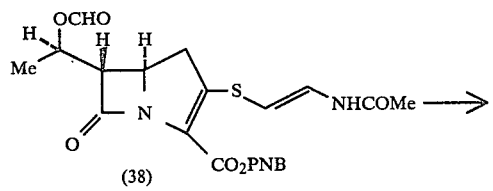

(38)

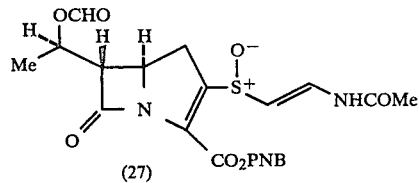

(27)

A solution of the formate (38) (228 mg) in 20% aqueous dioxan (30 ml) was stirred with m-chloroperbenzoic acid (108 mg) at 5° for 30 min. The solution was diluted with ethyl acetate (50 ml) and the organic layer was washed with dil. NaHCO$_3$ solution (50 ml) water (50 ml) and brine (30 ml). Evaporation of the dried (MgSO$_4$) solution gave a foamy residue (177 mg) which consisted of the title sulphoxide diastereoisomers (27).

EXAMPLE 33

(i) 2-Carbamoylethenylthioacetate

HC≡C—CONH$_2$ + CH$_3$COSH ⟶

CH$_3$COS—CH=CH—CONH$_2$ + CH$_3$COS—CH=CH—CONH$_2$

Propiolamide (640 mgs) in dry dimethylformamide (DMF), (5 ml) was treated with potassium carbonate (13.8 mgs) and thiolacetic acid (705 mgs) with cooling. After 30 mins t.l.c. analysis (ethyl acetate) showed absence of starting material. The solution was diluted with ethyl acetate (50 ml) and washed with brine (3×50 ml). The organic layer was dried and the solvent removed to give a brown semi-solid product. This was chromatographed on silica gel 60 (Merck Art 7729; 230–400 ASTM) eluting with ethyl acetate:hexane, 1:1. The first product, on trituration with ether, gave Z-2-carbamoylethenylthioacetate as a colourless solid, 207 mg (15%). $v_{max}$. (CHCl$_3$) 3525, 3410, 1705, 1680, and 1590 cm$^{-1}$. δ(d6-acetone) 2.43 (3H, s, CH$_3$CO—), 6.29 (1H, d, J 10 Hz; COCH=), 7.55 (1H, d, J 10 Hz; =CH.S), ~6.1–7.8 (2H, v. broad s, —NH$_2$).

The second component was E-2-carbamoylethenyl-thioacetate isolated as a solid, 130 mgs. (10%). $v_{max}$. 3525, 3410, 1710, 1680 and 1590 cm$^{-1}$ δ(d6-acetone) 2.47 (3H, s, CH$_3$CO—), 6.35 (1H, d, J 16 Hz; —COCH=), 7.94 (1H, d, J 16 Hz; =CH S—), ~6.1–7.5 (2H, v. broad s, —NH$_2$).

(ii) p-Nitrobenzyl 3-[E-2-carbamoylethenylthio]-6-[1-p-nitrobenzyloxycarbonyloxyethyl]-7-oxo-1-azabicyclo[3.2.0]hept-2-ene-2-carboxylate

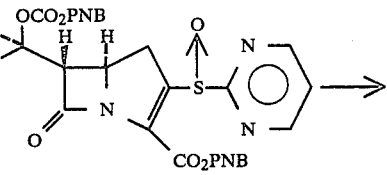

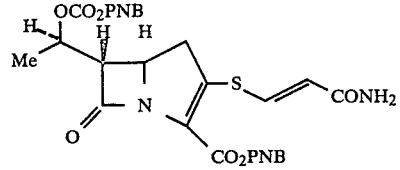

E-2-Carbamoylethenylthioacetate (23 mgs) in dioxan (3 ml) was treated with an aqueous solution of 0.1M sodium hydroxide (3.2 ml). After 15 min. at ambient temperature, the dioxan was removed in vacuo and a further quantity of water (3 ml) was added.

This solution was added to a solution of p-nitrobenzyl 3-[pyrimidin-2-ylsulphinyl]-6-[1-p-nitrobenzyloxycarbonyloxyethyl]-7-oxo-1-azabicyclo[3.2.0]hept-2-ene-2-carboxylate (100 mg) in dichloromethane (6 ml), at 0° C. Cetyldimethylbenzylammonium chloride (1 mg) was added and the mixture vigorously stirred. After ca. 12 hrs t.l.c. analysis (ethyl acetate:ethanol, 9:1) showed reaction had proceeded to completion. The mixture was diluted with dichloromethane and the organic phase separated, dried and solvent removed to give an off-white solid upon trituration with ether. Chromatography on silica gel 60 (Merck Art. 7729; 230–400 ASTM) eluting with ethyl acetate:hexane; 3:1, gave p-nitrobenzyl 3-[E-2-carbamoylethenylthio]6-[1-p-nitrobenzyloxycarbonyloxyethyl]-7-oxo-1-azabicyclo[3.2.0]hept-2-ene-2-carboxylate (15 mgs; 15%) as a white solid. $v_{max}$. (CHCl$_3$), 1790, 1745, 1690(b), 1610, 1590, 1560, 1525 and 1350 cm$^{-1}$; δ(d6-acetone), 1.45 (3H, d, J 6 Hz; —CH$_3$), 3.48 (1H, dd, J 8, 18 Hz; C4—H), 3.59 (1H, dd, J 10, 18 Hz; C4—H), 3.83 (1H, dd, J 3, 6 Hz; C6—H), 4.45 (1H, m, C5—H), 5.22 (1H, dt, J 7, 14 Hz; C8—H), 5.35 (2H, s, —OCO$_2$CH$_2$Ph), 5.55 (2H, ABq, —CO$_2$CH$_2$Ph), 6.38 (1H, d, J 17 Hz; =CH.CONH$_2$), 6.46 (1H, broad s, —NH—), 7.00 (1H, broad s, —NH—), 7.65 (1H, d, J 17 Hz; —SCH=), 7.68 and 7.78 (4H, d, J 9 Hz; arom —H), 8.25 and 8.26 (4H, d, J 9 Hz; arom —H).

EXAMPLE 34 p-Nitrobenzyl 3-[Z-2-carbamoylethenylthio]-6-[1-p-nitrobenzyloxy carbonyloxyethyl]-7-oxo-1-azabicyclo[3.2.0]hept-2-ene-2-carboxylate

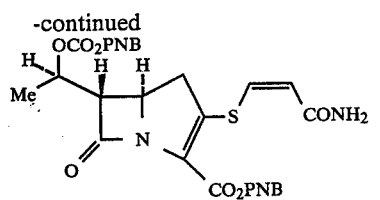

Z-2-Carbamoylethenylthioacetate (23 mgs) in dioxan (3 ml) was treated with an aqueous solution of 0.1M sodium hydroxide (3.2 ml). After 30 mins at ambient temperature the dioxan was removed in vacuo and a further 3 ml of water added.

This solution was added to a solution of p-nitrobenzyl-3-[pyrimidin-2-ylsulphinyl]-6-[1-p-nitrobenzyloxycarbonyloxyethyl]-7-oxo-1-azabicyclo[3.2.0]hept-2-ene-2-carboxylate (100 mg) in dichloromethane (6 ml) at 0° C. Cetyldimethylbenzylammonium chloride (1 mg) was added. After stirring vigorously for 30 mins at 0° C. and ca 12 hrs at ambient temperature, t.l.c. analysis (ethyl acetate) showed completion of reaction. The phases were partitioned and the aqueous phase extracted with dichloromethane. The organic phases were combined, dried and the solvent removed. Chromatography on silica gel 60 (Merck Art. 7729; 230–400 ASTM) eluting with ethyl acetate, gave a yellow solid, which, upon trituration with acetone/ether gave a white solid shown to be p-nitrobenzyl 3-[Z-2-carbamoylethenylthio]-6-[1-p-nitrobenzyloxycarbonyloxyethyl]-7-oxo-1-azabicyclo[3.2.0]hept-2-ene-2-carboxylate (15 mgs; 15%). $\nu_{max}$. 1795, 1745, 1690(b), 1605, 1590, 1560, 1525 and 1350 cm$^{-1}$; δ(d6-DMSO) 1.36 (3H, d, J 7 Hz; —CH$_3$), 3.41–3.62 (m, 2CH—H masked by H$_2$O), 3.89 (1H, dd, J 3, 6 Hz; C6—H), 4.29 (1H, m, C5—H), 5.00 (1H, quint., J 6 Hz; C8—H), 5.33 (2H, s, —OCO$_2$CH$_2$Ph), 5.44 (2H, ABq, —CO$_2$CH$_2$Ph), 6.58 (1H, d, J 10 Hz; =CHCO—), 7.65 and 7.76 (4H, d, J 9 Hz; arom —H), 7.72 (1H, d, J 10 Hz; —SCH=), 8.24 (4H, d, J 9 Hz; arom—H).

EXAMPLE 35

Sodium 3-[E-2-carbamoylethenylthio]-6-[1-hydroxyethyl]-7-oxo-1-azabicyclo[3.2.0]hept-2-ene-2-carboxylate

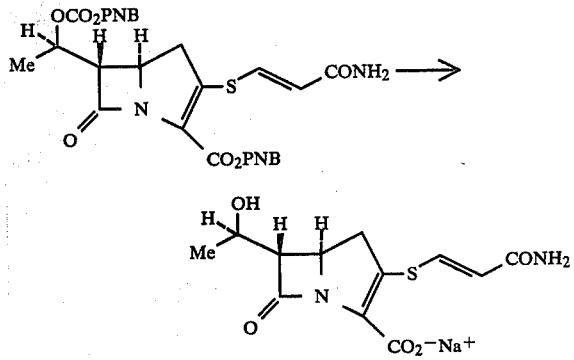

10% Palladium/charcoal catalyst (15 mg), suspended in 50% aqueous dioxan (4 ml) was pre-hydrogenolysed for 20 mins. To this was then added a solution of p-nitrobenzyl 3-[E-2-carbamoylethenyl thio]-6-[1-p-nitrobenzyloxycarbonyloxyethyl]-7-oxo-1-azabicyclo[3.2.0]hept-2-ene-2-carboxylate (11 mg) in 50% aqueous dioxan (6 ml). After hydrogenolysis for 2½ hr., sodium hydrogen carbonate (1.5 mg) in water (1 ml) was added. The dioxan was removed in vacuo and the aqueous phase extracted with ethyl acetate. The aqueous solution was shown to contain 3.75 mgs; (65%), of sodium 3-[E-2-carbamoylethenylthio]-6-[1-hydroxyethyl]-7-oxo-1-azabicyclo[3.2.0]hept-2-ene-2-carboxylate, $\nu_{max}$. (H$_2$O) 316 nm.

EXAMPLE 36

(i) Preparation of 2-(5-Methyltetrazol-1-yl)ethylthiol

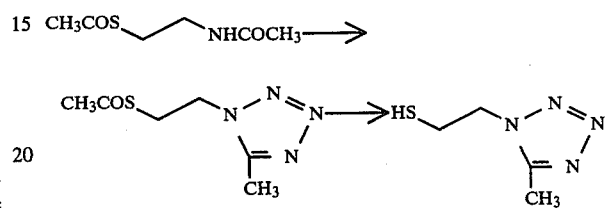

N,S-Diacetyl β-mercaptoethylamine, (805 mg) in dichloromethane (16 ml) was treated with N-methylmorpholine (3.3 ml). The reaction mixture was cooled to −40° and treated with phosgene (8.7 ml, 12.5% solution in toluene, d. 0.91; 990 mg COCl$_2$). After warming to room temperature tetramethylguanidinium azide (1.0 g) in dichloromethane (10 ml) was added. After stirring for 15 min. the reaction mixture was washed with water (2×20 ml), dried (MgSO$_4$) and evaporated in vacuo. Toluene was added to the residue and evaporated in vacuo to remove residual N-methylmorpholine. The crude product was chromatographed on silica gel (230–400 mesh ASTM, 2.5×12 cm column) eluting with ethyl acetate to give 2-(5-methyltetrazol-1-yl)ethyl thioacetate (767 mg), λ$_{max}$. (CH$_2$Cl$_2$) 1 795, 1 530, 1 410, 1 360, 1 135, 1 110, 1 080 and 940 cm$^{-1}$., δ(CDCl$_3$) 2.30 (3H,s), 2.68 (3H,s), 3.40 (2H, t, J ca 7.5 Hz), 4.54 (2H, t, J ca 7.5 Hz). 2-(5-methyltetrazol-1-yl)ethyl thioacetate (100 mg) was suspended in 0.1M aqueous NaOH (11 ml) and the mixture was stirred vigourously under argon at room temperature. After ca 15 min. the oil seemed to have dissolved. After 30 min. the solution was neutralised to pH 7 by addition of dilute HCl. The solution was then extracted with ethyl acetate (2×20 ml) and the extract dried (MgSO$_4$) and evaporated in vacuo. Toluene (20 ml) was added and evaporated in vacuo. The residue was taken up in dichloromethane (20 ml). Evaporation in vacuo left the thiol as an oil (31 mg), $\nu_{max}$. (CH$_2$Cl$_2$) 3 050, 2 950, 2 850 (broad), 1 530, 1 410, 1 320, 1 110, 1 085 cm$^{-1}$., δ(CDCl$_3$) 1.51 (1H, broad s), 2.65 (3H,s), 3.12 (2H, broad t, J ca 6 Hz), 4.51 (2H, t, J 6.5 Hz) ppm. Found M+ m/e 144.046 7; C$_4$H$_8$N$_4$S requires m/e 144.046 9.

(ii) Preparation of p-Nitrobenzyl (5RS, 6SR)-6-[(1RS)-1-p-Nitrobenzyloxycarbonyloxyethyl]-3-[2-(5-methyltetrazol-1-yl)ethylthio]-7-oxo-1-azabicyclo[3.2.0]hept-2-ene-2-carboxylate

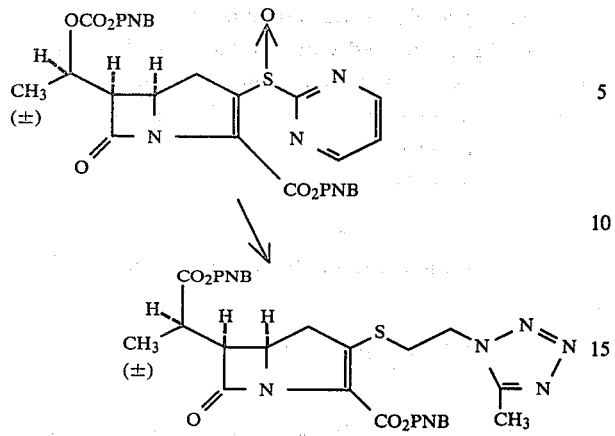

p-Nitrobenzyl (5RS, 6SR)-6-[(1RS)-1-p-nitrobenzyloxycarbonyloxyethyl]-3-(2-pyrimidylsulphinyl)-7-oxo-1-azabicyclo[3.2.0]hept-2-ene-2-carboxylate (136 mg) in dichloromethane (5 ml) was cooled in an icebath, treated with benzyldimethyl-n-hexadecylammonium chloride (4 mg) followed by 2-(5-methyltetrazol-1-yl)ethylthiol (29 mg), followed by 0.1M aqueous sodium hydroxide (2.1 ml). The mixture was stirred vigourously for 45 min, then allowed to warm to room temperature and stirred for a further 15 min. The mixture was diluted with dichloromethane (25 ml) and brine (25 ml). After separation the dichloromethane layer was dried (MgSO$_4$) and evaporated in vacuo. Chromatography on silica gel (2.5×12 cm., 230–400 mesh ASTM) eluting with ethyl acetate (200 ml) followed by ethyl acetate/ethanol (95:5) gave the title compound (64 mg), $\nu_{max.}$ (CH$_2$Cl$_2$) 1 790, 1 755, 1 710 and 1 610 cm$^{-1}$. $\delta$(CDCl$_3$) 1.48 (3H, d, J ca 6.5 Hz), 2.56 (3H, s), 2.83 (1H, dd, J 8 and 18 Hz), 3.06 (1H, dd, J 10 and 18 Hz), 3.25–3.52 (3H, m), 4.12 (1H, approx d t, J 2.5 and 10 Hz), 4.38–4.62 (2H, m), 5.05–5.20 (1H,m), 5.23 (1H,d, J 13 Hz), 5.28 (2H,s), 5.47 (1H, d, J 13 Hz), 7.58 (2H, d, J 9 Hz), 7.62 (2H, d, J 9 Hz), 8.23 (2H, d, J 9 Hz), 8.26 (2H, d, J 9 Hz) ppm.

EXAMPLE 37

Preparation of sodium (5RS, 6SR)-6-[(1RS)-1-Hydroxyethyl]-1-[2-(5-methyltetrazol-1-yl)ethylthio]-7-oxo-1-azabicyclo[3.2.0]hept-2-ene-2-carboxylate

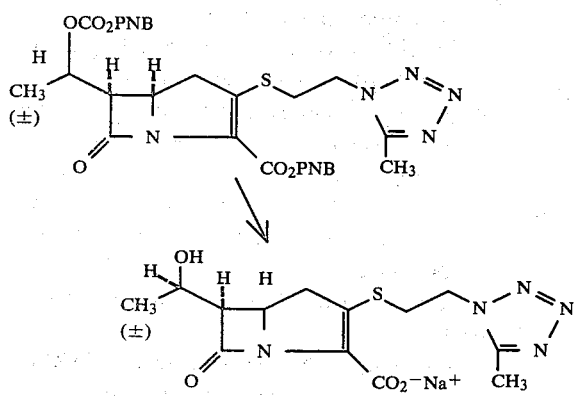

The ester from Example 36 (70 mg) in dioxan (12 ml) and water (6 ml) was hydrogenated over 5% Pd/C catalyst (120 mg) for 2.25 hr. Sodium hydrogen carbonate (9 mg) in water (2 ml) was added and the mixture was then filtered through Celite. The filter cake was washed with water (70 ml) and the combined filtrate and washings were evaporated in vacuo to ca 50 ml. The solution was then washed with ethyl acetate (3×150 ml), and then reduced in volume to ca 10 ml by evaporation in vacuo. The solution was loaded onto a column of DIAION HP-20 (2.5×10 cm) and the column eluted with water (300 ml), followed by water/ethanol mixtures; 95:5 (100 ml); 90:10 (100 ml).

The fractions were monitored by u.v. spectroscopy, fractions containing a maximum at ca 298 nm were combined, evaporated in vacuo to ca 10 ml and freeze-dried to give the title compound as a solid (20 mg), $\lambda_{max.}$ (H$_2$O) 298 ($\epsilon_{max.}$ 7 712) nm., $\nu_{max.}$ (KBr) 1 750, 1 595, 1 400 cm$^{-1}$. $\delta$(D$_2$O) 1.26 (3H,d,J 6 Hz), 2.58 (3H,s), 2.83 (1H, dd, J 9.5 and 18 Hz), 2.98 (1H, dd, J 10.5 and 18 Hz), 3.2–3.35 (2H, dd, J 3 and 6 Hz at $\delta$ 3.20 ppm superimposed on m), 3.38–3.50 (1H,m), 3.99 (1H, dt, J 3 and 10 Hz), 4.19 (1H, quintet, J 6 Hz), 4.57–4.75 (2H, m) ppm.

EXAMPLE 38

(i) Preparation of 1-(2-Acetylthioethyl)-5-Triphenylmethylaminomethyltetrazole

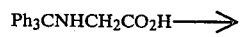
(a)

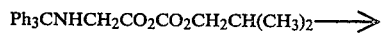
(b)

(c)

(d)

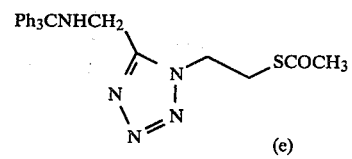

N-Tritylglycine (a) (1.06 g) was suspended in dichloromethane (25 ml) and treated with triethylamine (0.463 ml) followed by isobutylchloroformate (458 mg). After stirring for 1 hr. the solution of the mixed anhydride (b) was added to a suspension of 2-aminoethanethiol hydrochloride (379 mg) under argon which had been treated with triethylamine (0.463 ml). Pyridine (0.1 ml) was then added to the mixture. After 4 hr. triethylamine (0.463 ml), followed by acetyl chloride (0.237 ml) were added. After stirring for 1 hr. the solution was washed with water and evaporated to leave an oil which still contained a substantial quantity of thiol (c). This was taken up in tetrahydrofuran (5 ml) and treated with sodium hydride (160 mg, 50% dispersion in oil) followed by acetyl chloride (0.237 ml). After stirring under argon for 1 hr. ethyl acetate (30 ml) was added followed by brine (20 ml). The ethyl acetate layer was dried and evaporated and the residue chromatographed on silica gel (230–400 mesh ASTM, 3×15 cm) eluting with ethyl acetate/hexane mixtures 3:7(100 ml), 4:6 (300 ml), 1:1 this eventually gave two u.v. positive products, the second of which proved to be the thioacetate, (d) (567 mg), $\nu_{max}$. (CHCl$_3$) 3 375, 1 680 cm$^{-1}$., $\delta$(CDCl$_3$) 2.38 (3H,s), 2.54 (1H, s, exch D$_2$O), 2.99 (2H,s), 3.10 (2H, t, J ca 6 Hz), 3.3–3.6 (2H,m), 7.0–8.0 (16 H,m).

The thioacetate, (d) (560 mg) in dichloromethane (10 ml) was treated with N-methylmorpholine (1.0 ml), cooled to $-30°$ and then a solution of phosgene in toluene (2.5 ml, 12.5% w/w d 0.91), diluted with dichloromethane (7.5 ml) was added dropwise. The reaction was then allowed to warm to room temperature and stirred for 15 min. Tetramethylguanadinium azide in solution in dichloromethane (2.2 ml., 100 mg/ml) was then added and stirring was continued for 20 min. More of the solution of azide (0.7 ml) was added and after 3 min. the solution was extracted with water (2×50 ml), dried (MgSO$_4$) and evaporated in vacuo. The mixture was taken up in dichloromethane (20 ml), loaded onto a column of silica gel (230–400 mesh ASTM, 2.5×20 cm) and the column was eluted with ethyl acetate/hexane 4:6.

1-(2-Acetylthioethyl)-5-triphenylmethylaminomethyltetrazole was obtained, after evaporation in vacuo of relevant fractions, as a foam (298 mg), $\nu_{max}$. (CH$_2$Cl$_2$) 3 325 (broad), 1 695 cm$^{-1}$. $\delta$(CDCl$_3$) 2.21 (3H, s), 2.60 (1H, broad t, exch. D$_2$O) 3.28 (2H,t, J 7 Hz), 3.60 (2H, d, J 7 Hz, s on D$_2$O exch.), 4.35 (2H,t,J 7 Hz), 7.0–7.8 (15 H,m).

(ii) Preparation of 1-(2-Acetylthioethyl)-5-p-nitrobenzyloxycarbonylaminomethyltetrazole

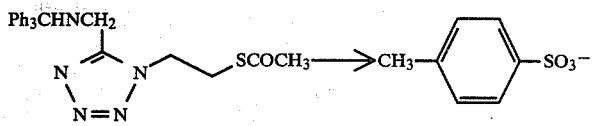

(e)

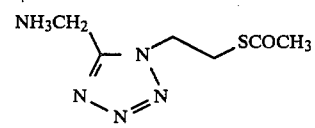

(f)

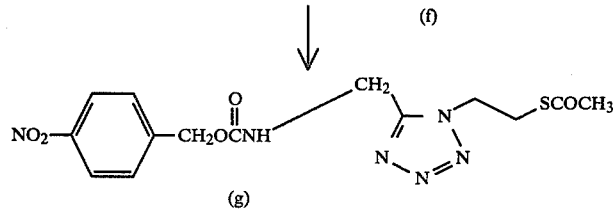

(g)

1-(2-Acetylthioethyl)-5-triphenylmethylaminomethyltetrazole, (e) (300 mg) in acetone (3 ml) was cooled to $-20°$ and treated with p-toluenesulphonic acid monohydrate (128 mg) in acetone (2 ml). The reaction mixture was allowed to warm to room temperature and stirred for 7 hours. The resultant colourless solid was filtered off to give the p-toluenesulphonic acid salt (f) (190 mg), m.p. 184°–185°, $\nu_{max}$ (KBr)1680, 1235, 1225, 1170, 1150, 1130, 1042, 1015, 838, 688, 572 cm$^{-1}$, (D$_2$O) 2.28 (3H,s), 2.35 (3H,s), 3.34 (2H, t, J Ca 6 Hz), 7.30 (2H, d, J 9 Hz), 7.65 (2H, d, J 9 Hz)ppm. Other signals were obscured by the HOD signal.

The salt (f) was suspended in dry CH$_2$Cl$_2$ (4 ml) at 0° and treated with p-nitrobenzylchloroformate (100 mg) in CH$_2$Cl$_2$ (1 ml), followed by triethylamine (0.128 ml). After 30 minutes further quantities of p-nitrobenzylchloroformate (20 mg) and triethylamine (0.025 ml) were added and stirring was continued for a further 30 minutes. The solution was then diluted with dichloromethane (20 ml) washed with water (10 ml), dried (MgSO$_4$) and evaporated. The crude product was chromatographed on silica gel (2.5×12 cm, 230–400 mesh ASTM) eluting with ethyl acetate/hexane mixtures; 4:6 (50 ml), 1:1 (50 ml), 6:4 (50 ml), 7:3 (50 ml) and then with ethyl acetate. Fractions containing the desired product were combined and evaporated to give 1-(2-acetylthioethyl)-5-p-nitrobenzyloxycarbonylaminomethyltetrazole (160 mg) $\nu_{max}$ (CH$_2$Cl$_2$)3430, 1730, 1690, 1520, 1350 cm$^{-1}$, $\delta$(CDCl$_3$) 2.33 (3H,s), 3.34 (2H, t, J Ca 6.5 Hz), 4.58 (2H, t, J Ca 6.5 Hz), 4.74 (2H, d, J 6 Hz), 5.20 (2H,s) 6.66 (1H, t, J Ca 6 Hz), 7.46 (2H, d), 8.14 (2H,d) ppm.

(iii) Preparation of p-Nitrobenzyl (5RS6SR)-[2-(5-p-Nitrobenzyloxycarbonylaminomethyltetrazol-1-yl)ethylthio]-6-[(1RS)-1-nitrobenzyloxycarbonyloxyethyl]-7-oxo-1-azabicyclo[3.2.0]hept-2-ene-2-carboxylate

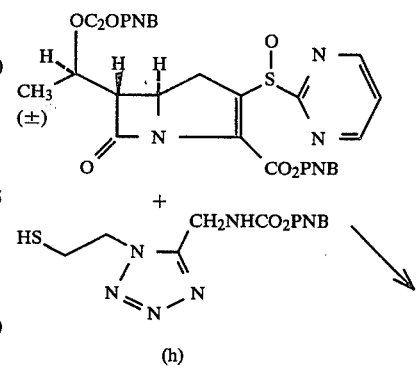

(h)

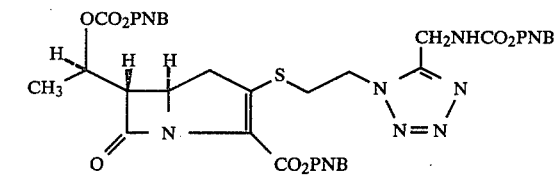

1-(2-Acetylthioethyl)-5-p-Nitrobenzyloxycarbonylaminomethyltetrazole (100 mg) in dioxan (0.5 ml) was treated with 0.1N NaOH (5.3 ml). After stirring under argon for 20 minutes the reaction mixture was neutralised to pH 7 by addition of dilute aqueous HCl. The mixture was diluted with H$_2$O (50 ml) and ethyl acetate (50 ml), after shaking and separation the ethyl acetate was dried (MgSO$_4$) and evaporated to give the thiol (h) $\nu_{max}$ (CH$_2$Cl$_2$) 3430, 1730, 1520, 1350, 1235 cm$^{-1}$. The thiol and the sulphoxide (170 mg) were dissolved in dichloromethane (20 ml) at 0° and treated with 0.1N NaOH (2.6 ml) and water (5 ml) followed by benzyldimethyl-n-hexadecylammonium chloride (4 mg). After 1 hour at 0° a further 6 mg of the ammonium chloride was added, followed by 0.1N NaOH (1 ml). After 5 minutes the solution was diluted with H$_2$O (20 ml) and dichloromethane (50 ml). The layers were separated and the dichloromethane layer was dried (MgSO$_4$) and evaporated in vacuo. Chromatography of the crude product on silica gel (230–400 mesh ASTM, 2.5×10 cm) eluting with ethyl acetate gave, after combination and evaporation in vacuo of the relevant fractions, the title compound (67 mg) $\nu_{max}$ (CH$_2$Cl$_2$) 3430, 1790, 1750 (sh), 1730, 1525, 1350 cm$^{-1}$.

EXAMPLE 39

(i) Preparation of (Z)-1-(5-Methyltetrazol-1-yl)-2-triphenylmethylthioethene

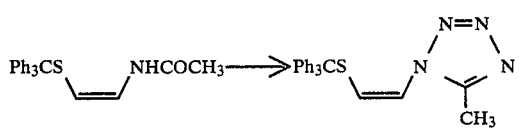

(Z)-1-Acetamido-2-triphenylmethylthioethene (1.07 g) in dry dichloromethane (30 ml) containing N-methylmorpholine (3.5 ml, 3.22 g) was cooled to −30° and treated with phosgene in toluene (8.4 ml, 12.5% w/w). After warming to room temperature and stirring for 30 minutes tetramethylguanidinium azide (600 mg) in dichloromethane (6 ml) was added. After 45 min. a further quantity of tetramethylguanidinium azide (300 mg) in dichloromethane was added. After a further 45 min. the reaction mixture was washed with water (2×300 ml), followed by saturated brine. After drying (MgSO$_4$) the dichloromethane was evaporated in vacuo. Toluene (30 ml) was added and evaporated in vacuo (2×) and the residual material was crystallised from ethyl acetate/hexane to give (Z)-1-(5-methyltetrazol-1-yl)-2-triphenylmethylthioethene (827 mg), m.p. 208°–210°, $\nu_{max}$ (CHCl$_3$) 1600, 1490, 1445, 1410 cm$^{-1}$., δ(CDCl$_3$) 2.54 (3H, s), 6.15 (1H, d, J 9 Hz), 6.59 (1H, d, J 9 Hz), 7.35 (15 H, s) p.p.m. (Found: C, 71.65; H, 5.20; N, 14.41%. C$_{23}$H$_{20}$N$_4$S requires C, 71.9; H, 5.21; N, 14.6%).

(ii) Preparation of Silver (Z)-2-(5-Methyltetrazol-1-yl)ethen-1-yl-thiolate

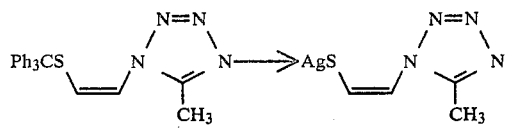

(Z)-1-(5-Methyltetrazol-1-yl)-2-triphenylmethylthioethene (709 mg) in methanol (100 ml) was heated under reflux until all had dissolved. Pyridine (0.18 ml, 176 mg) in methanol (5 ml) was added followed by silver nitrate (310 mg) in H$_2$O (14 ml) and methanol (7 ml). After heating under reflux for 3 min. the mixture was cooled and stirred at room temperature for 2 hours. The mixture was then centrifuged and the precipitate washed with methanol (2×50 ml) and ether (2×50 ml). After drying in vacuo the silver salt was obtained as a powder, $\nu_{max}$. (KBr) 3060, 3020, 2920, 1517, 1385, 1265, 1115, 853, 838, 725, 695 and 665 cm$^{-1}$.

(iii) Preparation of (Z)-2-(5-Methyltetrazol-1-yl)ethen-1-yl Thioacetate

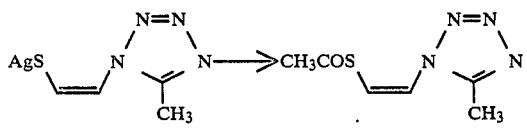

The silver thiolate (424 mg) in acetonitrile (8 ml) was treated with acetyl chloride (133 mg) in acetonitrile (1.3 ml). After 30 min the solution was diluted with ethyl acetate, filtered through Celite, and the solvents were then evaporated in vacuo. Toluene (20 ml) was added to the residue and evaporated in vacuo (2×). The residue was chromatographed on silica gel (230–400 mesh ASTM) (2.5×15 cm) eluting with ethyl acetate to yield (Z)-2-(5-methyltetrazol-1-yl)ethen-1-yl thioacetate (65 mg). Crystallisation from ethyl acetate/hexane gave colourless plates m.p. 135°–137°, $\nu_{max}$. (CH$_2$Cl$_2$) 1715, 1635, 1520, 1410 cm$^{-1}$. δ (CDCl$_3$) 2.51 (3H, s), 2.60 (3H, s), ca 6.9 (1H, d, J 8.5 Hz), ca 7.25 (1H, d J 8.5 Hz) p.p.m.

(iv) Preparation of p-Nitrobenzyl (5RS, 6SR)-3-[(Z)-2-(5-Methyltetrazol-1-yl)ethen-1-yl]thio-6-[(1RS)-p-Nitrobenzyloxycarbonyloxyethyl]7-oxo-1-azabicyclo[3.2.0]hept-2-ene-2-carboxylate.

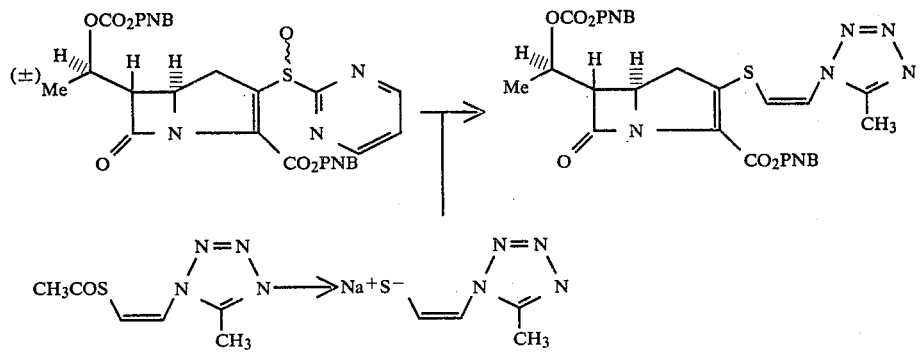

The thioacetate (50 mg) in dioxan (1 ml) under argon was cooled to 10° and treated with aq. 0.1N NaOH (5.4 ml). After 15 min. the reaction mixture was allowed to warm to room temperature and left to stand for 15 min.

T.l.c. indicated disappearance of starting material and the appearance of a zone on the origin, indicating formation of the sodium thiolate. The volume of the solution was reduced to ca. 3 ml by evaporation in vacuo in order to remove some doxan. Water (2 ml) was then added to the solution.

The sulphoxide (164 mg) in dichloromethane (7.5 ml) was treated with benzyldimethyl-n-hexadecylammonium chloride, cooled in an ice bath and then treated with the aqueous solution of the sodium thiolate. After stirring for 30 min. the solution was diluted with dichloromethane (50 ml) and brine (20 ml). The layers were separated and the dichloromethane dried (MgSO$_4$) and evaporated in vacuo. Chromatography of the product on silica gel, eluting with ethyl acetate (300 ml) followed by ethylacetate/ethanol (9:1) gave the title product 100 mg, $\nu_{max}$. (CH$_2$Cl$_2$) 1785, 1750, 1715 (sn), 1605, 1520, 1380, 1350 cm$^{-1}$. $\lambda_{max}$. (EtOH) 333 and 265 nm.

EXAMPLE 40

Preparation of Sodium (5RS,6RS)-6-[(1RS)-1-Hydroxyethyl]-3-[(Z)-2-(5-methyltetrazol-1-yl)ethenylthio]-7-oxo-1-azabicyclo[3.2.0]hept-2-ene-2-carboxylate

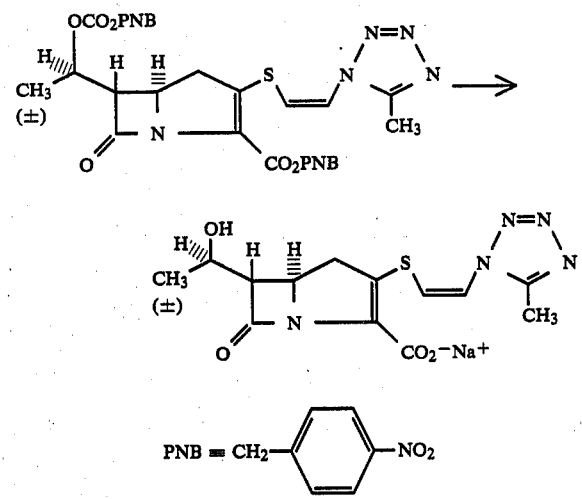

The ester (100 mg) in dioxan (15 ml) and water (7.5 ml) was hydrogenated over 5% Palladium or carbon catalyst (150 mg) for 2.5 hr. Sodium hydrogen carbonate (13 mg) in water (5 ml) was added and the catalyst was removed by filtration through Celite. The filter cake was washed with water (30 ml) and the volume of combined filtrate and washings were reduced to ca 30 ml. by evaporation in vacuo. The resultant solution was extracted with ethyl acetate (2×50 ml) and the aqueous solution then evaporated in vacuo to ca 10 ml and loaded onto a column of DIAION HP20 (2.5×10 cm). The column was eluted with water (300 ml), water/ethanol (9:1) (200 ml) followed by water/ethanol (8:2) (200 ml). The solution eluted by the aqueous ethanol contained the desired title sodium salt. If desired this solution can be evaporated in vacuo to a smaller volume and freeze dried to give the sodium salt $\lambda_{max}$. (H$_2$O) 313 nm.

EXAMPLE 41

Preparation of p-Nitrobenzyl (5RS,6SR)-3-(2-acetamidoethylthio)-6-[(1RS)-1-p-nitrobenzyloxycarbonyloxyethyl]-7-oxo-1-azabicyclo[3.2.0]hept-2-ene-2-carboxylate

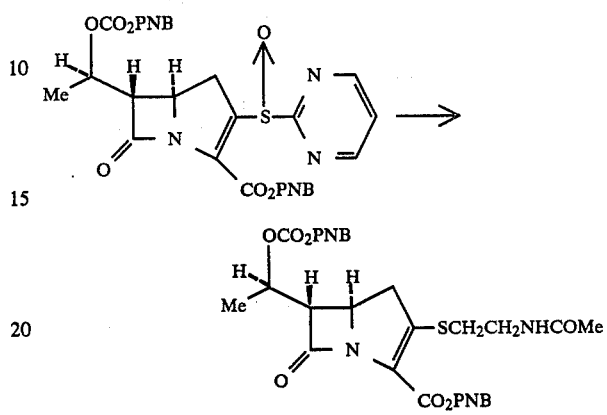

p-NItrobenzyl (5RS, 6SR)-6-[(1RS)-1-p-nitrobenzyloxycarbonyloxyethyl]-3-(2-pyrimidylsulphinyl)-7-oxo-1-azabicyclo[3.2.0]hept-2-ene-2-carboxylate (15 mg) in dichloromethane (2 ml) was cooled in an ice-bath and treated with benzyldimethyl-n-hexadecylammonium chloride (1.1 mg), followed by 2-acetamidoethanethiol (3 mg) in dichloromethane (1 ml), followed by water (1 ml), followed by 0.1M aqueous NaOH (0.25 ml). After stirring in the cold for 30 min. the reaction mixture was allowed to warm to room temperature and stirred for 1.5 h. After dilution with CH$_2$Cl$_2$/H$_2$O and separation, the dichloromethane layer was dried (MgSO$_4$) and evaporated in vacuo. The residue was chromatographed on silica gel, eluting with ethyl acetate, followed by ethylacetate/ethanol (95:5) to give the title compound $\nu_{max}$. (CH$_2$Cl$_2$) 3450, 1790, 1750, 1700(sh), 1680, 1525, 1350 cm$^{-1}$.

EXAMPLE 42

Preparation of p-Nitrobenzyl (5RS,6SR)-3-[Z-2-(2-p-nitrobenzyloxycarbonylaminoethyloxycarbonyl)ethenylthio]-6-[(1RS)-1-p-nitrobenzyloxycarbonyloxyethyl]-7-oxo-1-azabicyclo[3.2.0]hept-2-ene-2-carboxylate

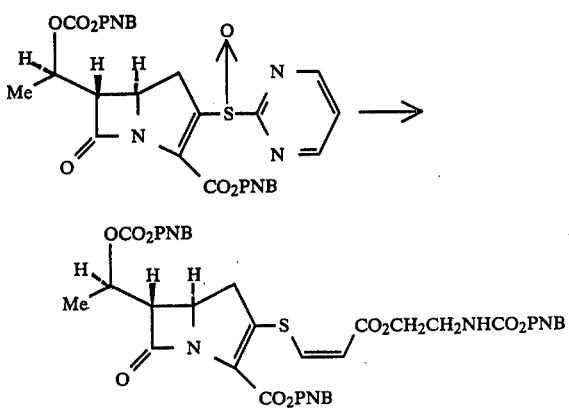

2-p-Nitrobenzyloxycarbonylaminoethyl Z-3-acetylthiopropenoate (52 mg) (prepared from thiolacetic acid and the corresponding propiolate) in dioxan (2 ml) was treated with 0.1M aqueous NaOH (2.8 ml) and the mixture was stirred for 30 min. Most of the dioxan was removed by evaporation in vacuo and water (1 ml) was added to the solution. The resultant solution of the sodium thiolate (contaminated by unchanged thioester) was added to a solution of p-nitrobenzyl (5RS,6SR)-6-[(1RS)-1-p-nitrobenzyloxycarbonyl)oxyethyl)]-3-(2-pyrimidinylsulphinyl)-7-oxo-1-azabicyclo[3.2.0]hept-2-ene-2-carboxylate (90 mg) and benzyldimethyl-n-hexadecylammonium chloride (7 mg) in dichloromethane (5 ml). The mixture was stirred at 0°. After 30 min 0.1M NaOH aqueous solution (1.0 ml) was added and stirring was continued at 0° for 30 min. After dilution with dichloromethane and brine the dichloromethane layer was dried (MgSO$_4$) and evaporated. Chromatography on silica gel (230–400 mesh ASTM) (2.5×12 cm) eluting with ethyl acetate/hexane mixtures; 1:1 (100 ml), 7:3 (100 ml) 8:2 (100 ml) 9:1 gave fractions containing the desired product. These were combined and evaporated to give the product as an oil (30 mg). This was rechromatographed on silica gel, eluting with ethyl acetate/hexane (7:3) to give the title compound, $v_{max}$. (CH$_2$Cl$_2$) 3450, 1790, 1730, 1525, 1350 cm$^{-1}$., δ (250 MHz) (CDCl$_3$) inter alia 1.41 (3H, d, J 6 Hz), 3.12 (1H, dd, J 8 and 17.5 Hz), 3.35–3.6 (4H, m), 4.2–4.4 (3H, m), 6.0 (1H, d, J 9.5 Hz) p.p.m.

We claim:

1. A process for the preparation of a compound of the formula (I):

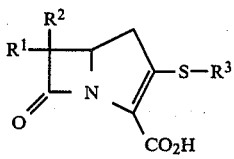

or a pharmaceutically acceptable salt or in-vivo hydrolysable ester thereof wherein $R^1$ and $R^2$ are each independently hydrogen, alkyl of 1 to 10 carbon atoms, alkenyl of up to 10 carbon atoms, alkynyl of up to 10 carbon atoms, cycloalkyl of 3 to 6 carbon atoms, cycloalkylalkyl of 3 to 6 carbon atoms in the cycloalkyl ring and 1 to 6 carbon atoms in the alkyl moiety, alkylcycloalkyl of 1 to 6 carbon atoms in the alkyl moiety and 3 to 6 carbon atoms in the cycloalkyl ring, phenyl, phenylalkyl of 1 to 6 carbon atoms in the alkyl moiety or phenylalkynyl of up to 6 carbon atoms in the alkynyl moiety each of which is unsubstituted or substituted by amino, mono-, di or tri-alkylamino of 1 to 6 carbon atoms in each alkyl moiety, hydroxyl, alkoxyl of 1 to 6 carbon atoms, mercapto, alkylthio of 1 to 6 carbon atoms in the alkyl moiety, phenylthio, sulfamoyl, amidino, guanidino, nitro, chloro, bromo, fluoro, cyano or carboxy, or one of $R^1$ and $R^2$ is hydrogen and the other is sulphonato-oxyethyl and $R^3$ is alkyl of 1 to 6 carbon atoms, alkenyl of 2 to 6 carbon atoms, alkynyl of 2 to 6 carbon atoms, phenyl, phenylalkyl of 1 to 6 carbon atoms in the alkyl moiety, alkanoyl of 1 to 6 carbon atoms, phenylalkanoyl of 1 to 6 carbon atoms in the alkyl moiety, phenylcarbonyl, heterocyclyl of 4 to 7 ring atoms up to 4 of which are selected from the group consisting of oxygen, sulphur and nitrogen, unsubstituted or substituted by one or more amino, alkanoylamino of 1 to 6 carbon atoms in the alkyl moiety, mono-, di- or tri-alkylamino of 1 to 6 carbon atoms in each alkyl moiety, hydroxyl, alkoxy of 1 to 6 carbon atoms, mercapto, alkylthio of 1 to 6 carbon atoms in the alkyl moiety, phenylthio, sulphamoyl, carbamoyl, amidino, guanidino, nitro, chloro, bromo, fluoro, carboxy, a carboxyl salt or a carboxyl ester, alkanoyloxy of 1 to 6 carbon atoms in the alkyl moiety or phenylcarbonyl; which process comprises reacting a compound of the formula (II):

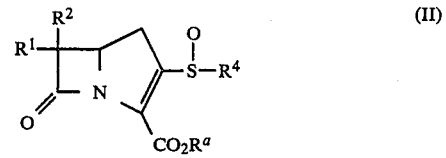

wherein $R^a$ is hydrogen, a salt moiety, RHU 1 and $R^2$ are as above defined, and $R^4$ is pyrimidinyl, with a compound of the formula (III):

wherein $R^3$ is as above defined, and thereafter if necessary:

(i) removing any group $R^a$,
(ii) converting the product into a pharmaceutically acceptable salt or in-vivo hydrolysable ester.

2. A process according to claim 1 when performed in the presence of a phase-transfer catalyst.

3. A process according to claim 1 or claim 2 when performed in dimethylformamide.

4. A process according to claim 1 in the presence of a base.

5. A process according to claim 1 wherein the amount of the compound of the formula (III) or reactive derivative thereof is between 1.0 to 1.5 moles per mole equivalent of the compound of the formula (II).

6. A process according to claim 1 wherein $R^3$ is alkyl of 1 to 6 carbon atoms, phenyl, pyrimidyl or pyridyl unsubstituted or substituted by amino, alkanoylamino of 1 to 6 carbon atoms in the alkyl moiety, carboxy or a salt or ester thereof, mono- or dialkylamino of 1 to 6 carbon atoms in each alkyl moiety, hydroxy or alkoxy of 1 to 6 carbon atoms; or alkenyl of 2 to 6 carbon atoms unsubstituted or substituted by alkanoylamino of 1 to 6 carbon atoms in the alkyl moiety or carboxy or a salt or ester thereof.

7. A process according to claim 1 wherein $R^a$ is benzyl, p-methoxybenzyl, 2,4,6-trimethylbenzyl, 3,5-di-t-butyl, 4-hydroxybenzyl, benzoylmethl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl or —N=CHR° wherein R° is phenyl.

8. A process according to claim 1 wherein CO$_2$R$^a$ is an in-vivo hydrolyzable ester moiety.

9. A process according to claim 1 wherein $R^a$ is a metal salt cation.

10. A process according to claim 1 wherein $R^a$ is an alkali metal salt cation.

11. A process according to claim 1 wherein $R^a$ is a tertiary amine salt cation.

12. A process according to claim 1 wherein $R^a$ is a silver, mercuric, lithium, sodium, triethylamine, N-ethylpiperidine or dimethylpiperazine cation.

13. A process according to claim 1 wherein the reaction temperature is ambient.

14. A process according to claim 1 wherein the reaction temperature is from 20° C. to −70° C.

15. A process according to claim 1 wherein the reaction temperature is from 0° C. to −50° C.

16. A process according to claim 2 wherein the reaction temperature is between 0° C. and ambient.

* * * * *